United States Patent [19]

Stach

[11] 4,314,840
[45] Feb. 9, 1982

[54] CYCLIC ACETAL-METHYL-CARBAMOYL-METHYL ESTERS OF PHOSPHONIC AND PHOSPHORIC ACIDS, AS HERBICIDES

[75] Inventor: Leonard J. Stach, Riverside, Ill.

[73] Assignee: Velsicol Chemical Corporation, Chicago, Ill.

[21] Appl. No.: 164,719

[22] Filed: Jun. 30, 1980

Related U.S. Application Data

[62] Division of Ser. No. 61,132, Jul. 26, 1979, Pat. No. 4,237,056.

[51] Int. Cl.³ .................... A01N 43/24; A01N 43/30; A01N 43/32
[52] U.S. Cl. .......................................... 71/87; 71/86; 424/203; 424/202
[58] Field of Search ..................................... 71/86, 87

[56] References Cited

U.S. PATENT DOCUMENTS 3,136,784 6/1964 Beriger ............................. 260/340.7
3,247,223 4/1966 Walsh et al. .................. 260/340.9 R
3,317,561 5/1967 Levey et al. .................. 260/340.9 R
3,627,784 12/1971 Dornach et al. ..................... 260/338

Primary Examiner—Anton H. Sutto
Attorney, Agent, or Firm—Dietmar H. Olesch; Robert J. Schwarz

[57] ABSTRACT

This invention discloses new compounds of the formula

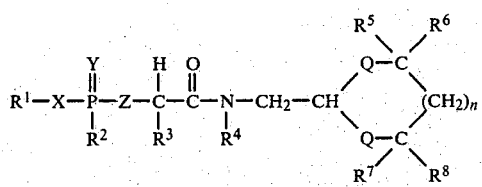

wherein X,Y,Z and Q are each independently selected from the group consisting of oxygen and sulfur; $R^1$ is selected from the group consisting of alkyl, and

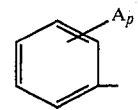

wherein A may be different at different positions and is selected from the group consisting of alkyl, alkoxy, alkylthio, halogen, nitro and cyano, p is an integer from 0 to 5; $R^2$ is selected from the group consisting of alkyl, alkoxy, alkylthio, amino, alkylamino, dialkylamino and

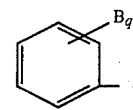

wherein B may be different at different positions and is selected from the group consisting of alkyl, alkoxy, alkylthio, halogen, nitro and cyano, and q is an integer from 0 to 5; $R^3$ is selected from the group consisting of hydrogen, alkyl and

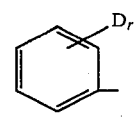

wherein D may be different at different positions and is selected from the group consisting of alkyl, alkoxy, alkylthio, halogen, nitro and cyano, and r is an integer from 0 to 5; $R^4$ is selected from the group consisting of hydrogen, alkyl cycloalkyl and

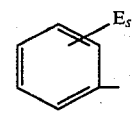

wherein E may be different at different positions and is selected from the group consisting of alkyl, alkoxy, alkylthio, halogen, nitro and cyano, and s is an integer from 0 to 5; $R^5$, $R^6$, $R^7$, and $R^8$ are each independently selected from the group consisting of hydrogen and alkyl; and n is an integer from 0 to 3.

Further disclosed are herbicidal and insecticidal compositions utilizing the aforedescribed compounds.

2 Claims, No Drawings

CYCLIC ACETAL-METHYL-CARBAMOYL-METHYL ESTERS OF PHOSPHONIC AND PHOSPHORIC ACIDS, AS HERBICIDES

This is a division of application Ser. No. 61,132, filed July 26, 1979, now U.S. Pat. No. 4,237,056.

This invention relates to new compositions of matter and more specifically relates to new chemical compounds of the formula

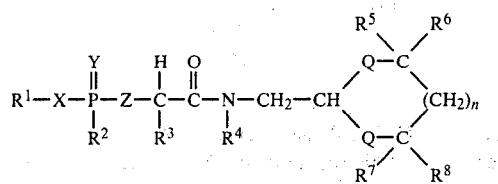

wherein X,Y,Z and Q are each independently selected from the group consisting of oxygen and sulfur; $R^1$ is selected from the group consisting of alkyl, and

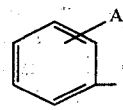

wherein A may be different at different positions and is selected from the group consisting of alkyl, alkoxy, alkylthio, halogen, nitro and cyano, and p is an integer from 0 to 5; $R^2$ is selected from the group consisting of alkyl, alkoxy, alkylthio, amino, alkylamino, dialkylamino and

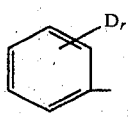

wherein B may be different at different positions and is selected from the group consisting of alkyl, alkoxy, alkylthio, halogen, nitro and cyano, and q is an integer from 0 to 5; $R^3$ is selected from the group consisting of hydrogen, alkyl and

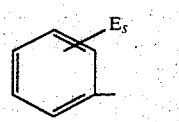

wherein D may be different at different positions and is selected from the group consisting of alkyl, alkoxy, alkylthio, halogen, nitro and cyano, and r is an integer from 0 to 5; $R^4$ is selected from the group consisting of hydrogen, alkyl, cycloalkyl and

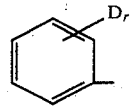

wherein E may be different at different positions and is selected from the group consisting of alkyl, alkoxy, alkylthio, halogen, nitro and cyano, and s is an integer from 0 to 5; $R^5, R^6, R^7$ and $R^8$ are each independently selected from the group consisting of hydrogen and alkyl; and n is an integer from 0 to 3.

The compounds of the present invention are useful as herbicides and insecticides.

In a preferred embodiment of this invention X,Y,Z and Q are independently selected from the group consisting of oxygen and sulfur; $R^1$ is selected from the group consisting of lower alkyl and

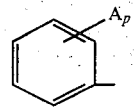

wherein A may be different at different positions and is selected from the group consisting of lower alkyl, lower alkoxy, lower alkylthio, halogen, nitro and cyano, and p is an integer from 0 to 5; $R^2$ is selected from the group consisting of lower alkyl, lower alkoxy, lower alkylthio, amino, lower alkylamino, lower dialkylamino and

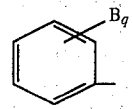

wherein B may be different at different positions and is selected from the group consisting of lower alkyl, lower alkylthio, halogen, nitro and cyano, and q is an integer from 0 to 5; $R^3$ is selected from the group consisting of hydrogen, lower alkyl and

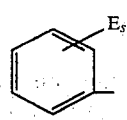

wherein D may be different at different positions and is selected from the group consisting of lower alkyl, lower alkoxy, lower alkylthio, halogen, nitro and cyano and r is an integer from 0 to 5; $R^4$ is selected from the group consisting of hydrogen, lower alkyl, lower cycloalkyl, and

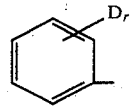

wherein E may be different at different positions and is selected from the group consisting of lower alkyl, lower alkoxy, lower alkylthio, halogen, nitro and cyano and s is an integer from 0 to 5; $R^5$, $R^6$, $R^7$ and $R^8$ are each independently selected from the group consisting of hydrogen and lower alkyl; and n is an integer from 0 to 3.

The term "lower" as used herein designates a straight or branched carbon chain or a carbocycle of up to six carbon atoms.

The compounds of the present invention can be prepared by reacting a compound of the formula

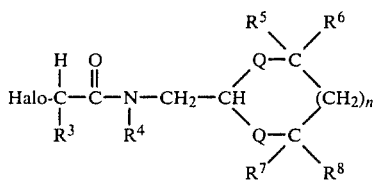 (II)

wherein $R^3$, $R^4$, $R^5$, $R^6$, $R^7$, $R^8$, Q and n are as heretofore described and Halo is a halogen such as chlorine or bromine, with about an equimolar amount of a phosphorous compound of the formula

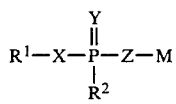 (III)

wherein $R^1$, $R^2$, X, Y and Z are as hereinbefore described and M is an alkali metal such as sodium or potassium or is ammonium. This reaction can be effected by combining the compound of formula II and III in an inert organic reaction medium such as acetonitrile at room temperature and then stirring the resulting mixture at a temperature of from room temperature to that of reflux for a period of from 2 to 24 hours. After this time, the reaction mixture is filtered to remove the halide salts and the filtrate is stripped of solvent to yield the desired product as a residue. This product can be used as such or can be further purified by standard techniques in the art.

The compounds of formula II can be prepared by reacting a compound of formula

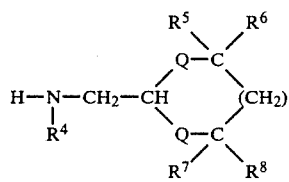 (IV)

wherein $R^4$, $R^5$, $R^6$, $R^7$, $R^8$, Q and n are as heretofore described, with a 2-haloalkanoyl chloride of formula

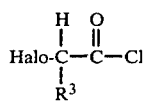 (V)

wherein $R^3$ and Halo are as heretofore described. This reaction can be effected by combining a compound of formula IV with about an equimolar or slightly excess molar amount of a compound of formula V in an inert organic reaction medium, such as toluene or methylene chloride, in the present of an acid acceptor such as an alkali metal carbonate or bicarbonate or a tertiary amine such as triethylamine, at a temperature of from about −10° C. to about 25° C. and stirring the resulting mixture for a period of from about 0.25 to 2 hours. After this time, the reaction mixture can be washed with water to remove inorganic salts and stripped of solvent to yield the desired product. This product can then be used as such or further purified by coventional means.

The compounds of formula IV can be prepared by reacting an amine of formula

 (VI)

wherein $R^4$ is as heretofore described, with a compound of the formula

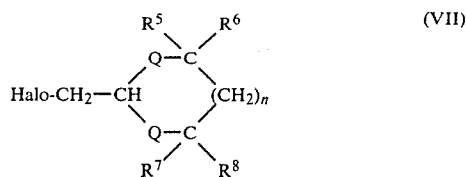 (VII)

wherein $R^5$, $R^6$, $R^7$, $R^8$, Q, n and Halo are as heretofore described. This reaction can be effected by combining the compound of formula VII with an excess molar amount of the amine of formula VI and heating the mixture with agitation for a period of from ½ to 8 hours. When a very low boiling amine is used a pressurized vessel can be preferably utilized. After this time strong inorganic base such as aqueous sodium hydroxide is added to the reaction mixture to liberate the free amine from its hydrochloride. The organic phase is then separated from the aqueous phase, dried over anhydrous magnesium sulfate and distilled to yield the desired product.

The compounds of formula VII can be prepared by reacting an acetal of formula

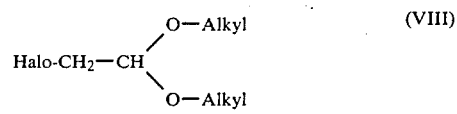 (VIII)

wherein Halo is as heretofore described and the alkyl is methyl or ethyl, with a diol, meraptoalcohol or dithiol of the formula

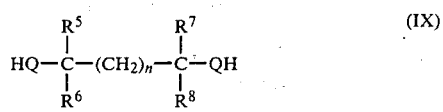 (IX)

wherein $R^5$, $R^6$, $R^7$, $R^8$, Q and n are as heretofore described. This reaction can be effected by combining about equimolar amounts of the compounds of formula VIII and IX under anhydrous conditions and in the presence of an acid catalyst such as sulfuric acid or toluenesulfonic acid. The mixture can be heated for a period of from 1 to about 4 hours at a temperature of from about 100° to 120° C. and the byproduct alcohol removed as it is formed. At the conclusion of the reaction, as indicated by cessation of alcohol evolution, the acid may be neutralized with sodium carbonate and the desired product isolated and purified by conventional techniques such as extraction, disstillation and the like. If the product is to be distilled from the reaction mixture, to prevent possible decomposition, it is preferable to remove the sodium carbonate before starting the distillation.

The compound of formula II may also be made by the reaction sequence.

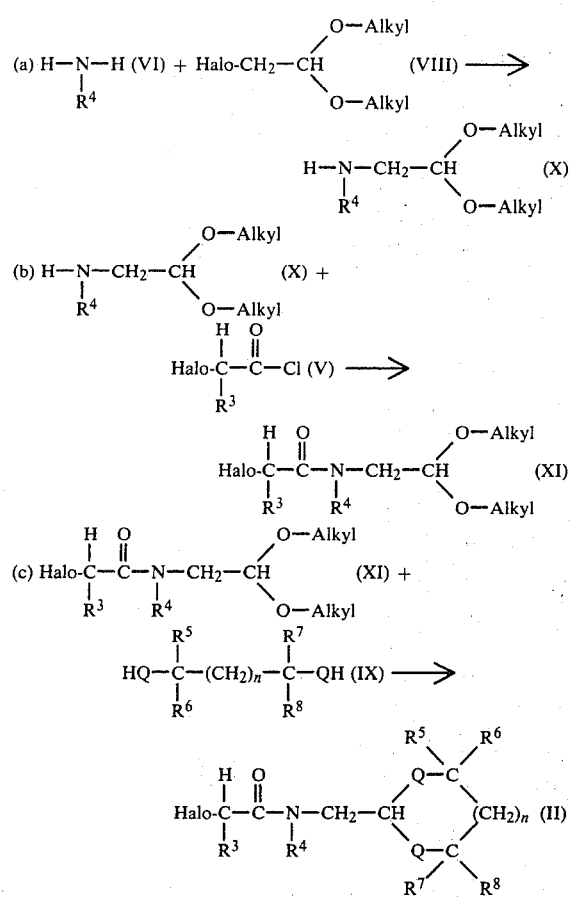

wherein Halo, alkyl, $R^3$, $R^4$, $R^5$, $R^6$, $R^7$, $R^8$, Q and n are as described heretofore. The compound of formula X may be made by reacting approximately equimolar amounts of the amine of formula VI with the compound of formula VIII. This reaction can be effected by combining the reactants in an inert reaction medium such as methylene chloride in the presence of an acid acceptor. The reaction mixture can be heated at reflux for a period of from 2 to 24 hours. After this time, the mixture is filtered and stripped of solvent to yield the desired product.

The compound of formula XI may be prepared by reacting the compounds of formulae X and V in the same manner as described hereinabove for the reaction between compound IV and V.

The compound of formula II can then be prepared by reacting the compounds of formula XI and IX in the same manner as described hereinabove for the reaction between the compounds of formula VIII and IX.

The compounds of formula III are known in the art.

Exemplary haloalkanoyl chlorides of formula V suitable for preparing compounds of the present invention are 2-chloropropanoyl chloride, 2-chloro-2-phenylethanoyl chloride, 2-chloro-2-(3-methylphenyl)ethanoyl chloride, 2-chloro-2-[2-(ethylthio)phenyl]ethanoyl chloride, 2-chloro-2-(2,5-dibromophenyl)ethanoyl chloride, 2-chloropentanoyl chloride, 2-chloro-2-(3,4-dinitrophenyl)ethanoyl chloride, 2-chloro-2-(2-cyanophenyl)ethanoyl chloride and the like.

Exemplary amines of formula VI suitable for preparing compounds of the present invention are methanamine, butanamine, cyclopropanamine, 3-nitrobenzenamine, 2-chlorobenzenamine, 3,4-dimethoxybenzenamine, 3-(ethylthio)benzenamine, 4-cyanobenzenamine, and the like.

Exemplary diols, mercaptoalcohols and dithiols of formula IX suitable for preparing compounds of the present invention are 1,2-ethanediol; 2,4-pentanediol; 2,6-heptanediol; 2,5-dimethyl-2,5-hexanediol. 2-Methyl-2,6-octanediol; 2-mercaptnethanol; 3-mercaptopropanol; 3-mercapto-4-methylhexanol; 6-mercapto-6-methyl-3-octanol; 6-mercapto-2-octanol; 5-mercaptoheptanol; 1,4-butanedithiol; 1,2-ethanedithiol; 2,6-nonanedithiol; 3,5-heptanedithiol, and the like.

The manner in which the compounds of the present invention can be prepared is more specifically illustrated in the following examples.

EXAMPLE 1

PREPARATION OF N-METHYL-N-(2,2-DIMETHOXYETHYL)-2-CHLOROACETAMIDE

N-Methyl-2,2-dimethoxyethanamine (50.0 grams; 0.42 mole), methylene chloride (200 ml) and triethylamine (46.6 grams; 0.462 mole) were charged into a glass reaction vessel fitted with a mechanical stirrer, and thermometer. A calcium chloride filled drying tube was attached and the solution was cooled to about −20° C. Chloroacetyl chloride (49.7 grams; 0.44 moles) dissolved in methylene chloride (25 ml) was then added dropwise, with stirring, while holding the temperature at about −20° C. to −10° C. At the end of the addition, stirring was continued at −20° C. to 10° C. for a period of about 1 hour. The solution was allowed to warm to room temperature, then was stirred at this temperature for a period of about 16 hours. Diethyl ether (125 ml) was then added and the resulting solution filtered. The filtrate was washed with water (30 ml). The washed filtrate was dried and filtered. The solvent was distilled off under mild heat and reduced pressure to yield a residue which was fractionally distilled under reduced pressure to yield the desired product N-methyl-N-(2,2-dimethoxyethyl)-2-chloroacetamide as a fraction boiling at 112° C.–119° C. at 0.30 mm. Hg.

EXAMPLE 2

PREPARATION OF N-(1,3-DIOXOLAN-2-YLMETHYL)-N-METHYL-2-CHLOROACETAMIDE

N-Methyl-N-(2,2-dimethoxyethyl)-2-chloroacetamide (19.5 grams; 0.10 mole), ethylene glycol (6.82 grams; 0.11 mole) and 10 drops of a solution of one gram of p-toluenesulfonic acid in 100 ml of diethyl ether were charged into a glass reaction vessel fitted with a mechanical stirrer, thermometer, distillation head and condenser. The mixture was stirred and heated to about 100° C. to 110° C. Byproduct methanol was distilled off. When no further methanol was evolved, the mixture was cooled to room temperature, sodium carbonate (2 grams) was added and the slurry was stirred for a period of about 1 hour. The slurry was then filtered and the filtrate fractionally distilled under reduced pressure. The desired product N-(1,3-dioxolan-2-ylmethyl)-N-methyl-2-chloroacetamide was obtained as a fraction boiling at 124° C. at 0.30 mm Hg and at 119° C. at 0.15 mm Hg.

EXAMPLE 3

PREPARATION OF O,O-DIETHYL S-[N-METHYL-N-(1,3-DIOXOLAN-2-YLMETHYL)CARBAMOYLMETHYL]PHOSPHOROTHIOLOTHIONATE

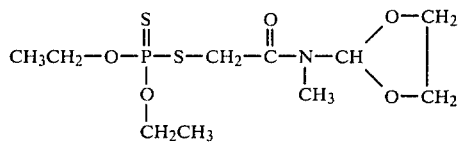

N-(1,3-Dioxolan-2-ylmethyl)-N-methyl-2-chloroacetamide (3.0 grams; 0.015 mole), acetonitrile (70 ml) and S-potassium O,O-diethyl phosphorothiolothionate (4.03 grams; 0.018 mole) were charged into a glass reaction vessel fitted with a mechanical stirrer, thermometer and reflux condenser. The reaction mixture was stirred and refluxed for a period of about 9 hours. It was then cooled to room temperature and filtered. The solids filtered off were washed with methylene chloride and these washings were combined with the filtrate. Solvent was stripped from the combined solution by mild warming under reduced pressure. The residue was dissolved in methylene chloride (80 ml), washed with three portions of water, dried over magnesium sulfate and filtered. The solvent was stripped from the filtrate by mild warming under reduced pressure. The residue was then subjected to a vacuum of 0.10 mm Hg and temperature of 50° C. for a period of about 5 minutes to yield the desired product O,O-diethyl S-[N-methyl-N-(1,3-dioxolan-2-ylmethyl)carbamoylmethyl]-phosphorothiolothionate as a pale yellow oil. Elemental analysis; Theory: C=38.47%; H=6.46%; N=4.08%; P=9.02%; S=18.67%; Found: C=38.50%; H=6.44%; N=3.68%; P=9.77%; S=20.28%.

EXAMPLE 4

PREPARATION OF O,O-DIMETHYL S-[N-METHYL-N-(1,3-DIOXOLAN-2-YLMETHYL)CARBAMOYLMETHYL] PHOSPHOROTHIOLOTHIONATE

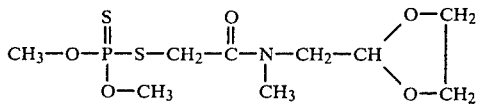

N-(1,3-Dioxolan-2-ylmethyl)-N-methyl-2-chloracetamide (3.50 grams; 0.018 mole), acetonitrile (50 ml) and S-ammonium O,O-dimethyl phosphorothiolothionate (3.5 grams; 0.02 mole) were charged into a glass reaction vessel fitted with a mechanical stirrer, thermometer and reflux condenser. The reaction mixture was stirred and refluxed for a period of about 8 hours. It was then cooled to room temperature and filtered. The solids filtered off were washed with methylene chloride and these washings were combined with the filtrate. Solvent was stripped from the combined solution by mild warming under reduced pressure. The residue was dissolved in methylene chloride (60 ml), washed with two portions of water, dried over magnesium sulfate and filtered. The solvent was stripped from the filtrate by mild warming under reduced pressure. The residue was then subjected to a temperature of about 50° C. under a vacuum of 0.1 mm Hg for a period of about 5 minutes to yield the desired product O,O-dimethyl S-[N-methyl-N-(1,3-dioxolan-2-ylmethyl)carbamoylmethyl]phosphorothiolothionate as a pale yellow oil. Elemental analysis; Theory: C=34.28%; H=5.75%; N=4.44%; P=9.82%; S=20.34%; Found: C=33.79%; H=5.76%; N=4.54%; P=9.49%; S=20.21%.

EXAMPLE 5

PREPARATION OF O-METHYL S-[N-METHYL-N-(1,3-DIOXOLAN-2-YLMETHYL)CARBAMOYLMETHYL]N-(1-METHYLETHYL)PHOSPHORAMIDOTHIOLATE

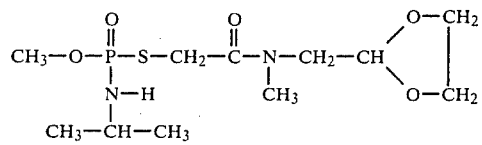

N-(1,3-Dioxolan-2-ylmethyl)-N-methyl-2-chloroacetamide (3.0 grams; 0.015 mole), acetonitrile (60 ml) and S-potassium N-(1-methylethyl)phosphoramidothiolate (3.42 grams; 0.0165 mole) were charged into a glass reaction vessel fitted with a mechanical stirrer, thermometer and reflux condenser. The reaction mixture was stirred and refluxed for a period of about 8 hours. It was then cooled to room temperature and filtered. The solids filtered off were washed with methylene chloride and these washings were combined with the filtrate. Solvent was stripped from the combined solution by mild warming under reduced pressure. The residue was dissolved in methylene chloride (70 ml), washed with three portions of water, dried over magnesium sulfate and filtered. The solvent was stripped from the filtrate by mild warming under reduced pressure. The residue was then subjected to a temperature of 50° C. under a vacuum of 0.10 mm Hg for a period of about 5 minutes to yield the desired product O-methyl S-[N-methyl-N-(1,3-dioxolan-2-ylmethyl)carbamoylmethyl]N-(1-methylethyl)phosphoramidothiolate Elemental analysis; Theory: C=40.48%; H=7.10%; N=8.58%; P=9.49%; S=9.83%; Found: C=40.62%; H=7.38%; N=8.42%; P=9.14%; S=10.32%.

EXAMPLE 6

PREPARATION OF O-ETHYL S-PROPYL S-[N-METHYL-N-(1,3-DIOXOLAN-2-YLMETHYL)CARBAMOYLMETHYL]PHOSPHORODITHIOLATE

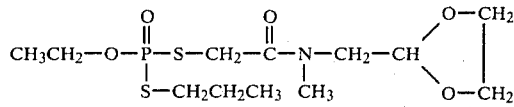

N-(1,3-Dioxolan-2-ylmethyl)-N-methyl-2-chloroacetamide (1.93 grams; 0.01 mole), acetonitrile (50 ml) and S-potassium S-propyl O-ethyl phosphorodithiolate (2.38 grams; 0.01 mole) were charged into a glass reaction vessel fitted with a mechanical stirrer and thermometer. This reaction mixture was stirred at room temperature for a period of about 16 hours. It was then filtered. The solvent was removed from the filtrate by mild warming under reduced pressure. The residue was dissolved in ethyl acetate and this solution washed with water then dried over sodium sulfate. The ethyl acetate was removed by mild warming under reduced pressure; the residue was then held at about 0.1 mm Hg pressure at room temperature for a period of about 2 hours to yield the desired product O-ethyl S-propyl S-[N-(1,3-dioxolan-2-ylmethyl)carbamoylmethyl]phosphorodithiolate as a pale brown oil. Elemental analysis; Theory: C=40.32%; H=6.77%; N=3.92%; P=8.67%; Found: C=39.33%; H=6.92%; N=4.32%; P=7.96%.

EXAMPLE 7

PREPARATION OF O,S-DIETHYL S-[N-METHYL-N-(1,3-DIOXOLAN-2-YLMETHYL)CARBAMOYLMETHYL]PHOSPHORODITHIOLATE

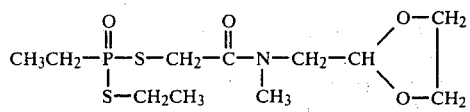

N-(1,3-Dioxolan-2-ylmethyl)-N-methyl-2-chloracetamide (1.93 grams; 0.01 mole), acetonitrile (50 ml) and S-potassium S-ethyl O-ethyl phosphorodithiolate (2.60 grams; 0.01 mole) were charged into a glass reaction vessel fitted with a mechanical stirrer and thermometer. This reaction mixture was stirred at room temperature for a period of about 16 hours and then filtered. The solvent was removed from the filtrate by mild warming under reduced pressure. The residue was dissolved in ethyl acetate and this solution washed with water then dried over sodium sulfate. The ethyl acetate was removed by mild warming under reduced pressure; the residue was then held at about 0.1 mm Hg pressure at room temperature for a period of about 2 hours to yield the desired product O,S-diethyl S-[N-methyl-N-(1,3-dioxolan-2-ylmethyl)carbamoylmethyl]phosphorodithiolate. Elemental analysis; Theory: C=38.47%; H=6.46% N=4.08%; P=9.02% S=18.67%; Found: C=38.49%; H=6.48% N=4.22; P=8.06%; S=17.69%.

EXAMPLE 8

PREPARATION OF N-(2,2-DIMETHOXYETHYL)-2-CHLOROACETAMIDE 2,2-Dimethoxyethananamine (36.93 grams; 0.35 moles), methylene chloride (200 ml) and triethylamine (37.1 grams; 0.367 moles) were charged into a glass reaction vessel fitted with a mechanical stirrer, and thermometer. A calcium chloride filled drying tube was attached and the solution was cooled to about $-20°$ C. Chloroacetyl chloride (41.47 grams; 0.367 moles) dissolved in methylene chloride (50 ml) was then added dropwise, with stirring, while holding the temperature at about $-10°$ C. to $0°$ C. At the end of the addition, stirring was continued at $0°$ C. for a period of about 2 hours. The solution was allowed to warm to room temperature then stirred at this temperature for 16 hours. It was then filtered and the solvent removed by mild warming under reduced pressure. The residue was dissolved in diethyl ether (100 ml) and the resulting solution filtered. The diethyl ether was then stripped from the filtrate by mild warming under reduced pressure and the residue was vacuum distilled. The desired product N-(2,2-dimethoxyethyl)-2-chloroacetamide was collected at a boiling point of $94°$ CC.$-95°$ C. at 0.25 mm Hg.

EXAMPLE 9

PREPARATION OF N-(1,3-DIOXOLAN-2-YLMETHYL)-2-CHLOROACETAMIDE

N-(2,2-Dimethoxyethyl)-2-chloroacetamide (18.1 grams; 0.10 mole) ethylene glycol (6.82 grams; 0.11 mole) and 10 drops of a solution of one gram of p-toluenesulfonic acid in 100 ml of diethyl ether were charged into a glass reaction vessel fitted with a mechanical stirrer, thermometer, distillation head and condenser. The mixture was stirred and heated to about $95°$ C. to $100°$ C. Byproduct methanol was distilled off. When no further methanol was evolved, the mixture was cooled to room temperature, sodium carbonate (2 grams) was added and the slurry was stirred for a period of about 1 hour. The slurry was then filtered and the filtrate fractionally distilled under reduced pressure the desired product N-(1,3-dioxolan-2-ylmethyl)-2-chloroacetamide was obtained as a fraction boiling at $109°$ C.$-110°$ C. at 0.15 mm Hg which, when cooled, solidfied. The solid had a melting point of $61°$ C.$-63°$ C.

EXAMPLE 10

PREPARATION OF O-ETHYL S-PROPYL S-[N-(1,3-DIOXOLAN-2-YLMETHYL)-CARBAMOYLMETHYL]PHOSPHORODITHIOLATE

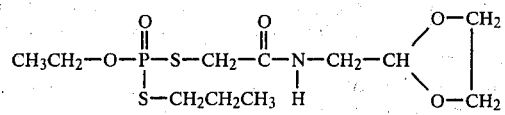

N-(1,3-Dioxolan-2-ylmethyl)-2-chloroacetamide (3.05 grams; 0.017 mole) acetonitrile (50 ml) and S-potassium S-propyl O-ethyl phosphorodithiolate (4.76 grams; 0.02 mole) were charged into a glass reaction vessel fitted with a mechanical stirrer, thermometer and reflux condenser. The reaction mixture was stirred and refluxed for a period of about 2 hours. It was then cooled to room temperature and filtered. Solvent was stripped from the solution by mild warming under reduced pressure. The residue was dissolved in methylene chloride (50 ml), washed with two portions of water, dried over magnesium sulfate and filtered. The solvent was stripped from this filtrate by mild warming under reduced pressure. The residue was then subjected to a temperature of about $60°$ C. under a vacuum of 0.2 mm Hg for a period of about 5 minutes to yield the desired product O-ethyl S-propyl S-[N-(1,3-dioxolan-2-ylmethyl)carbamoylmethyl]phosphorodithiolate as a white oil. Elemental analysis: Theory: C=38.47%; H=6.46%; N=4.08%; P=9.02%; S=18.67%; Found: C=38.30%; H=6.59%; N=4.10%; P=8.58%; S=18.02%.

EXAMPLE 11

PREPARATION OF N-(1,3-DIOXAN-2-YLMETHYL)-2-CHLORACETAMIDE

N-(2,2-Dimethoxyethyl)-2-chloroacetamide (18.2 grams; 0.1 mole), 1,3-propanediol (7.61 grams; 0.1 mole) and 10 drops of a solution of 1 gram of toluenesulfonic acid in 100 ml of diethyl ether were charged into a glass reaction vessel fitted with a mechanical stirrer, thermometer, distillation head and condenser. The mixture was stirred and heated at about 120° C. for a period of about 1 hour while byproduct methanol was distilled off. The mixture was cooled to room temperature, sodium carbonate (2 grams) was added, and the slurry stirred for a period of about 1 hour. The slurry was filtered and the filtrate was stripped of solvent by mild warming under reduced pressure to yield the desired product N-(1,3-dioxan-2-ylmethyl)-2-chloracetamide as a residue.

EXAMPLE 12

PREPARATION OF O-ETHYL S-PROPYL S-[N-(1,3-DIOXAN-2-YLMETHYL)CARBAMOYL-METHYL]PHOSPHORODITHIOLATE

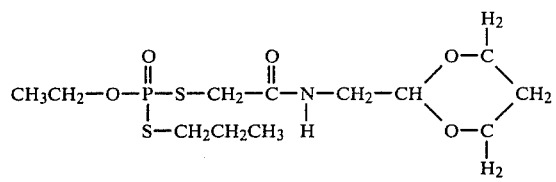

N-(1,3-Dioxan-2-ylmethyl)-2-chloracetamide (1.93 grams; 0.01 mole), acetonitrile (50 ml) and S-potassium S-propyl O-ethyl phosphorodithiolate (2.38 grams; 0.01 mole) were charged into a glass reaction vessel fitted with a mechanical stirrer and thermometer. This reaction mixture was stirred at room temperature for a period of about 16 hours and was then filtered. The solvent was removed from the filtrate by mild warming under reduced pressure. The residue was dissolved in ethyl acetate and this solution washed with water then dried over sodium sulfate. The ethyl acetate was removed by mild warming under reduced pressure; the residue was then held at about 0.1 mm Hg pressure at room temperature for a period of about 2 hours to yield the desired product O-ethyl S-propyl S-[N-(1,3-dioxan-2-ylmethyl)carbamoylmethyl]phosphorodithiolate. Elemental analysis; Theory: C=38.7%; H=6.51%; N=3.77%; P=8.34%; Found: C=40.88%; H=6.86%; N=4.75%; P=5.01%.

EXAMPLE 13

PREPARATION OF O,S-DIETHYL S-[N-(1,3-DIOXAN-2-YLMETHYL)CARBAMOYL-METHYL]PHOSPHORODITHIOLATE

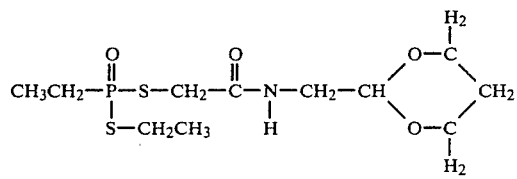

N-(1,3-Dioxan-2-ylmethyl)-2-chloroacetamide (1.93 grams; 0.01 mole), acetonitrile (50 ml) and S-potassium O,S-diethyl phosphorodithiolate (2.6 grams; 0.01 mole) were charged into a glass reaction vessel fitted with a mechanical stirrer and thermometer. This reaction mixture was stirred at room temperature for a period of about 16 hours. It was then filtered. The solvent was removed from the filtrate by mild warming under reduced pressure. The residue was dissolved in ethyl acetate and this solution washed with water then dried over sodium sulfate. The ethyl acetate was removed by mild warming under reduced pressure; the residue was then held at about 0.1 mm Hg pressure at room temperature for a period of about 2 hours to yield the desired product O,S-diethyl S-[N-(1,3-dioxan-2-ylmethyl)carbamoylmethyl]phosphorodithiolate. Elemental analysis; Theory: C=38.47%; H=6.46%; N=4.08%; P=9.02%; S=18.67%; Found: C=39.84%; H=6.85%; N=3.99%; P=6.88%; S=15.86%.

EXAMPLE 14

PREPARATION OF N-(4,5-DIMETHYL-1,3-DIOXOLAN-2-YL)-N-METHYL-2-CHLOROACETAMIDE

N-(2,2-Dimethoxyethyl)-N-methyl-2-chloroacetamide (97.8 grams; 0.5 mole), 2,3-butanediol (45 grams) and 0.2 grams p-toluenesulfonic acid were charged into a glass reaction vessel fitted with a mechanical stirrer, thermometer, distilling head and condenser. The reaction mixture was heated at about 90° C. to 100° for a period of 5 hours. Little reaction occurred as shown by the absence of methanol distilled. The reaction mixture was then heated at about 110° C., for about 2 hours at atmospheric pressure, then 1 hour at reduced pressure. Under these more rigorous conditions, methanol was formed and was distilled off. At the conclusion of the reaction, the reaction mixture was distilled and the fraction boiling at 127° C. to 130° C. at 0.55 mm Hg was the desired product N-(4,5-dimethyl-1,3-dioxolan-2-yl)-N-methyl-2-chloroacetamide.

EXAMPLE 15

PREPARATION OF O,O-Diethyl S-[N-METHYL-N-(4,5-DIMETHYL-1,3-DIOXO-LAN-2-YLMETHYL)CARBAMOYLMETHYL]-PHOSPHOROTHIOLOTHIONATE

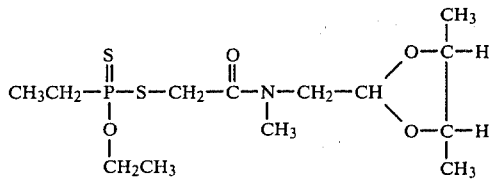

N-(4,5-Dimethyl-1,3-dioxolan-2-yl)-N-methyl-2-chloroacetamide (3.4 grams), S-potassium O,O-diethyl phosphorothiolothionate (4.1 grams) and acetonitrile (70 ml) were charged into a glass reaction vessel fitted with a mechanical stirrer and condenser. The reaction mixture was stirred at reflux for about 16 hours then allowed to cool to room temperature. The mixture was filtered, the solids filtered off were washed with methylene chloride (100 ml) and the washings combined with the filtrate. The solvents were stripped off by mild warming under reduced pressure. The residue was taken up in methylene chloride (80 ml). This solution was then washed with 3-20 ml portions of water, and dried over magnesium sulfate. The magnesium sulfate was filtered off and volatiles stripped from the filtrate by mild warming under reduced pressure to yield the desired product O,O-diethyl S-[N-methyl-N-(4,5-dimethyl-1,3-dioxolan-2-ylmethyl)-carbamoylmethyl]-phosphorothiolothionate as a yellow liquid. Elemental analysis; Theory: C=42.04%; H=7.06%; N=3.77%; P=8.34%; S=17.26%; Found: C=41.80%; H=7.00%; N=3.80%; P=8.10%; S=16.78%.

Additional compounds within the scope of the present invention can be prepared in a manner similar to that detailed in the foregoing examples. In the following examples are the essential ingredient to prepare the indicated named compounds by the procedures heretofore described.

EXAMPLE 16

S-Potassium S-(3-methylphenyl) N,N-dimethylphosphoramidodithiolate + N-cyclopropyl-N-(1,3-dioxepan-2-ylmethyl)-2-[[N-chloro-2-(4-methylphenyl-)acetamide = S-(3-methylphenyl) S-(1,3-dioxepan-2-ylmethyl)-N-cyclopropylcarbamoyl](4-methylphenyl)-methyl]N,N-dimethylphosphoramidodithiolate.

EXAMPLE 17

S-Potassium O-(4-ethoxyphenyl) ethylphosphonothiolothionate + N-(4,8-diethyl-1,3-dioxocan-2-ylmethyl)-2-(2-cyanophenyl)-2-chloroacetamide = O-(4-ethoxyphenyl) S-[N-(4,8diethyl-1,3-dioxocan-2-ylmethyl)carbamoyl](2-cyanophenyl)methyl]ethylphosphonothiolothionate.

EXAMPLE 18

S-Potassium O-[3-(ethylthio)phenyl]O-propyl phosphorothiolothionate + N-(3,5dipropyl-1,3-dioxan-2-ylmethyl)-2-[(4-ethylthio)phenyl]-2-chloroacetamide = O-[3-(ethylthio)-phenyl]O-propyl S-[[N-(3,5-dipropyl-1,3-dioxan-2-ylmethyl)carbamoyl][4-(ethylthio)-phenyl]methyl]phosphorothiolothionate.

EXAMPLE 19

S-Potassium O,S-dipentyl phosphorothiolothionate + N-(4-methyl-1,3-dioxolan-2-ylmethyl)-N-(3,5-dipropylphenyl)-2-chloroacetamide = O,S-dipentyl S-[N-(4-methyl-1,3-dioxolan-2-ylmethyl)-N-(3,5-dipropylphenyl)carbamoylmethyl]phosphorothiolothionate.

EXAMPLE 20

S-Potassium S-(3,5-dinitrophenyl) N-propylphosphoramidodithiolate + N-(1,3-dioxolan-2-ylmethyl)-2-(3-butoxyphenyl)-2-chloroacetamide = S-(3,5-dinitrophenyl) S-[[N-(1,3-dioxolan-2-ylmethyl)carbamoyl](3-butoxyphenyl)methyl]Npropylphosphoramidodithiolate.

EXAMPLE 21

S-Potassium O-phenyl O-propyl phosphorothiolothionate + N-(3,4-diethyl-1,3-dioxolan-2-ylmethyl)-N-(2,6-dinitrophenyl)-2-chloroacetamide = O-phenyl O-propyl S-[N(3,4-diethyl-1,3-dioxolan-2-ylmethyl)-N-(2,6-dinitrophenyl)carbamoylmethyl]phosphorothiolothionate.

EXAMPLE 22

O-Potassium S,S-dimethyl phosphorodithiolate + N-(1,3-dioxan-2-ylmethyl)-2-(4-nitrophenyl)-2-chloroacetamide = O-[[N-(1,3-dioxan-2-ylmethyl)carbamoyl](4-nitrophenyl)methyl]S,S-dimethyl phosphorodithiolate.

EXAMPLE 23

S-Potassium O-(2,6-dicyanophenyl) N,N-dibutylphosphoramidothiolothionate + N-(1,3-dioxepan-2-ylmethyl)-2-(3,4,5-triethoxyphenyl)-2-chloroacetamide = O-(2,6-dicyanophenyl)S-[[N-(1,3-dioxepan-2-ylmethyl)carbamoyl](3,4,5-triethoxyphenylmethyl]N,N-dibutylphosphoramidothiolothionate.

EXAMPLE 24

S-Potassium S-phenyl O-(3,4-dinitrophenyl) phosphorodithiolate + N-(1,3-dioxan-2-ylmethyl)-N-[3,4,5-tris(ethylthio)phenyl]-2-chloroacetamide = O-(3,4-dinitrophenyl) S-phenyl S-[N-(1,3-dioxan-2-ylmethyl)-N-[3,4,5-tris(ethylthio)phenyl]carbamoylmethyl]phosphorodithiolate.

EXAMPLE 25

S-Potassium O-phenyl pentylphosphonothiolothionate + N-(3,5-dihexyl-1,3-dioxan-2-ylmethyl)-N-(2,4,6-tricyanophenyl)-2-chloroacetamide = O-pentyl S-[[N-(3,5-dihexyl-1,3-dioxan-2-ylmethyl)-N-(2,4,6-tricyanophenyl)]carbamoylmethyl]pentylphosphonothiolothionate.

EXAMPLE 26

S-Potassium O,O-diethyl phosphorothiolate + N-(1,3-dioxolan-2-ylmethyl)-2-pentyl-2-chloracetamide = O,O-diethyl S-[[N-(1,3-dioxan-2-ylmethyl)carbamoyl](pentyl)methyl]phosphorothiolate.

EXAMPLE 27

S-Potassium S-methyl O-(3,4,5-trichlorophenyl) phosphorodithiolate + N-(1,3-dioxan-2-ylmethyl)-2-(3,4,5-trichlorophenyl) 2-chloro-acetamide = O-(3,4,5-trichlorophenyl) S-methyl S-[[N-(1,3-dioxan-2-ylmethyl)carbamoyl](3,4,5-trichlorophenyl)methyl]phosphorodithiolate.

EXAMPLE 28

S-Potassium S-methyl O-butyl phosphorodithiolothionate + N-(1,3-dioxolan-2-ylmethyl)-N-(2,4,6-tribromophenyl)-2-chloroacetamide = O-butyl S-methyl S[N-(1,3-dioxolan-2-ylmethyl)-N-(2,4,6-tribromophenyl)carbamoylmethyl]phosphorodithiolothionate.

EXAMPLE 29

S-Potassium O,O-dimethyl phosphorothiolothionate + N-(1,3-oxathiolan-2-ylmethyl)-2-chloropropanamide = O,O-dimethyl S-[[N-(1,3-oxathiolan-2-ylmethyl)carbamoyl](methyl)methyl]phosphorothiolothionate.

EXAMPLE 30

S-Potassium O,O-diethyl phosphorothiolate + N-methyl-N-(1,3-dithian-2-ylmethyl)-2-cyclohexyl-2-chloroacetamide = O,O-diethyl S-[[N-methyl-N-(1,3-dithian-2-ylmethyl)carbamoyl](cyclohexyl)methyl]phosphorothiolate.

EXAMPLE 31

S-Potassium S-propyl O-propyl phosphordithiolate + N-(1,3-dithiepan-2-ylmethyl)-2-chloracetamide + O-propyl S-propyl S-[N-(1,3-dithiepan-2-ylmethyl)carbamoylmethyl]phosphorodithiolate.

Additional compounds within the scope of the present invention which can be prepared by the procedures of the foregoing examples are; O,S-dihexyl S-[[N-(1,3-dioxolan-2-ylmethyl)-N-cyclohexylcarbamoyl](pentyl)methyl]phosphorothiolate; O-(3,5-dibutoxyphenyl) S-butyl S-[[N-(1,3-dioxan-2-ylmethyl)-N-phenylcarbamoyl](3,5-dinitrophenyl)methyl]phosphorothiolate; O-(2,6-dichloro-3-methylphenyl) O-ethyl S-[[N-(1,3- dioxolan-2-ylmethyl)carbamoyl](3,5-dichlorophenyl)-methyl]phosphorothiolate; O-(2,5-dicyanophenyl) O-[[N-(1,3-dioxepan-2-ylmethyl)-N-methylcarbamoyl](3,5-dimethoxyphenyl)methyl]N-pentylphosphoramidate; O-(4-nitrophenyl) O-[[N-(1,3-dioxoan-2-ylmethylcarbamoyl](3-cyano-4-methylphenyl)methyl]N,N-dipentylphosphoramidothionate; O-3,4-dibromo-5-propylphenyl) O-butyl O-[N-4-ethyl-5-propyl-1,3-dioxolan-2-ylmethyl)-N-(2,6-dicyano-4-nitrophenyl)carbamoylmethyl]phosphate; O-(4-cyanophenyl) O-ethyl O-[[N-(3,5-dibutyl-1,3-dioxan-2-ylmethyl)-N-(2,3,4,5,6-pentachlorophenylcarbamoyl][2-(ethylthio)phenyl]methyl]phosphorothionate; O-(4-chloro-2,6-dipropoxyphenyl) O-propyl S-[[N-(3-pentyl-1,3-dioxan-2-ylmethyl)-N-(3-ethoxyphenyl)carbamoyl](2,6-dibromophenyl)methyl]phosphorothiolate; O-[3,4,5-tris(1-methylethylthio)phenyl]O-[[N-(4,4,7,7-tetraethyl-1,3-dioxepan-2-ylmethyl)-N-(2-cyano-6-nitro)carbamoyl](2-cyanophenyl)methyl]S-butyl phosphorothiolothionate; O-propyl S-[[N-(4-butyl-1,3-dioxocan-2-ylmethyl)-N-(2,3,4,6tetrabromophenyl)carbamoyl](2,3-dinitrophenyl)methyl]propylphosphonothiolate; O-(2,5-dibromophenyl) O-[[N-(1,3-dioxolan-2-ylmethyl)-N-(3,5-dichloro-2,6-dimethoxyphenyl)carbamoyl]-phenylmethyl]butylphosphonothionate; O-(4-nitrophenyl) S-[N-cyclohexyl-N-(1,3-dithiolan-2-ylmethyl)carbamoylmethyl][bis(3,5-ethylthio)phenyl]phosphonothiolothionate; O-hexyl S-[[N-(4,6-dimethyl-1,3-dithian-2-ylmethyl)carbamoyl](ethyl)methyl](2-nitrophenyl)-phosphonothiolothionate; O-propyl S-[N-cyclopentyl-N-[1,3-dithiepan-2-ylmethyl)carbamoyl](3-chlorophenyl)methyl](3,5-dimethoxyphenyl)phosphonothiolothionate; O-(3,4,5-tricyanophenyl) S-ethyl S-[N-[(1,3-dithiocan-2-ylmethyl)carbamoyl](propyl)methyl]-phosphorodithiolothionate; O-(2,3,5,6-tetrachlorophenyl) S-[N-methyl-N-(1,3-oxathiolan-2-ylmethyl)carbamoylmethyl](3,4-dinitrophenyl)phosphonothiolothionate; O-hexyl S-[N-(4,6-dimethyl-1,3-oxathian-2ylmethyl)carbamoylmethyl](2,6-dichlorophenyl)phosphonothiolate; O-(1-methylpropyl) S-propyl S-[[N-(2,2-dimethylpropyl)-N-(1,3-oxathiocan-2-ylmethyl)carbamoyl](ethyl)methyl]phosphorodithiolate; O-ethyl S-[[N-(3,5-dimethoxyphenyl)-N-(4,8-dimethyl-1,3-oxathiocan-2-ylmethyl)carbamoyl](2,6-dinitrophenyl)methyl](5-ethylthio)phosphonothiolothionate.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under super-atmospheric pressure as aerosols. However, preferred liquid herbicidal compositions are emulsifiable concentrates which comprise an active compound according to this invention and as the inert carrier a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier sysems an inverted emulsion (water in oil) can be prepared for direct application to weed infestations.

A typical herbicidal composition according to this invention is illustrated by the following example, in which the quantities are in parts by weight.

EXAMPLE 32

Preparation of a Dust

Product of Example 3: 10
Powdered Talc: 90

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors, and the like in the herbicidal compositions heretofore described. These other materials can comprise from about 5% to about 95% of the active ingredients in the herbicidal compositions. Use of combinations these other herbicides and-/or defoliants, dessicants, etc. With the compounds of the present invention provide herbicidal compositions which are more effective in controlling weeds and often provide results unattainable with separate compositions of the individual herbicides. The other herbicides, defoliants, dessicants and the plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB) 2,4,-DEB, 4-CPB, 4-CPA, 4-CPP, 2,4,5-TB, 2,4,5-TES, 3,4-DA, silvex and the like; carbamate herbicides such as IPC, CIPC, swep barban, BCPC, CEPC, CPPC, and the like; thiocarbamate and dithiocarbamate herbicides such as CDEC, metham sodium, EPTC, diallate, PEBC, perbulate, vernolate and the like, substituted urea herbicides such as norea, siduron, dichloral urea, chloroxurn, cyculron, fenuron, monuron, monuron TCA, diuron, linuron, monlinuron, neburon, buturon, trimeturon and the like; symmetrical triazine herbicides such as simazine, chlorazine, atraone, desmetryne, norazine, ipazine, prometryn, atazine, trietazine, simetone, prometone, propazine, ametryne and the like; chloracetamide herbicides such as 4-(chloroacetyl)morpholine, 1-(chloroacetyl)-piperidine and the like; chlorinated aliphatio acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3, 6-dichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachlororterephthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulfide, AMS bromacil, 2-(3,4-dichlorphenyl)-4-methyl-1,2,4-oxadiazolidine, 3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like.

Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, wild buckwheat, kochia, medic, corn cockle, ragweed, sow-thistle, coffeeweed, croton, cuphea, dodder, fumitory, groundsel, hemp nettle, knawel, spurge, spurry, emex, jungle rice, pondweed, dog fennel, carpetweed, moringglory, bedstraw, ducksalad, naiad, cheatgrass, fall panicum, Jimsonweed, switchgrass, watergrass, teaweed, wild turnip and sprangletop; biennials such as wild carrot, matricaria, wild barley, campion, chamomile, burdock, mullein, roundleaved mallow, bull thistle, hounds-tongue, moth mullein and purple star thistle; or perennials such as white cockle, perennial ryegrass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail and winter-cress.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of active compound per acre may be required for good control of a dense infestation of hardy perennial weeds growing under favorable conditions.

The herbicidal toxicity of the new compounds of this invention can be illustrated by many of the established testing techniques known to the art, such as pre- and post-emergence testing.

The herbicidal activity of the compounds of this invention can be demonstrated by experiments carried out for the pre-emergence control of a variety of weeds. In these experiments small plastic greenhouse pots filled with dry soil are seeded with the various weed seeds. Twenty-four hours or less after seeding the pots are sprayed with water until the soil is wet and a test compound formulated as an aqueous emulsions of acetone solutions containing emulsifiers were sprayed at the indicated concentrations on the surface of the soil.

After spraying, the soil containers are placed in the greenhouse and provided with supplementary heat as required and daily or more frequent water. The plants are maintained under these conditions for a period of from 14 to 21 days, at which time the condition of the plants and the degree of injury to the plants is rated on a scale of from 0 to 10, as follows: 0=no injury, 1,2=slight injury, 3,4=moderate injury, 5,6=moderately severe injury, 7,8,9=severe injury and 10=death and N.E. no emergency to the plant. The effectiveness of these compounds is demonstrated by the data in Table 1 below.

The herbicidal activity of the compounds of this invention can also be demonstrated by experiments carried out for the post-emergence control of a variety of weeds. In these experiments the compounds to be tested are formulated as aqueous emulsions and sprayed at the desired dosage on the foliage of the weeds that have attained a prescribed size. After spraying the plants are placed in a greenhouse and watered daily or more frequently. Water is not applied to the foliage of the treated plants. The severity of the injury is determined 14 days after treatment and is reated on the scale of from 0 to 10 heretofore described. The effectiveness of these compounds is demonstrated by the data in Table 2 below.

For practical use as insecticides, the compounds of this invention are generally incorporated into insecticidal compositions which comprise an inert carrier and an insecticidally toxic amount of such a compound. Such insecticidal compositions, which can also be called formulations, enable the active compound to be applied conveniently to the site of the insect infestation in any desired quantity. These compositions can be solids, such as dusts, granules or wettable powders; or they can be liquids such as solutions, aerosols or emulsifiable concentrates.

For example, dusts can be prepared by grinding and blending the active compound with a solid inert carrier such as the talcs, clays, silicas, pyrophyllite and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water and/or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of insecticides can be dispersed under superatmospheric pressure as aerosols. However, preferred liquid insecticidal compositions are emulsifiable concentrates, which comprise an active compound according to this invention and as the inert carrier, a solvent and an emulsifier. Such emulsifiable concentrates can be extended with compound for application as sprays to the site of the insect infestation. The emulsifiers most commonly used in these concentrates are nonionic or mixtures of nonionic with anionic surface-active agents.

A typical insecticidal composition according to this invention is illustrated by the following example, in which the quantities are in parts by weight.

EXAMPLE 33

PREPARATION OF A DUST

Product of Example 3: 10
Powdered Talc: 90

The above ingredients are mixed in a mechanical grinder-blender and are ground until a homogeneous, freeflowing dust of the desired particle size is obtained. This dust is suitable for direct application to the site of the insect infestation.

The compounds of this invention can be applied as insecticides in any manner recognized by the art. One method for destroying insects comprises applying to the locus of the insect infestation, an insecticidal composition comprising an inert carrier and, as the essential active ingredient, in a quantity which is toxic to said insects, a compound of the present invention. The concentration of the new compounds of this invention in the insecticidal compositions will vary greatly with the type of formulation and the purpose for which it is designed, but generally the insecticidal compositions will comprise from about 0.05 to about 95 percent by weight of the active compound. The compositions can also comprise such additional substances as other pesticides, stabilizers, spreaders, deactivators, adhesives, stickers, fertilizers, activators, synergists and the like.

The compounds of the present invention are also useful when combined with other insecticides in the insecticidal compositions heretofore described. These other insecticides can comprise from about 5 to 95 percent of the active ingriedents in the insecticidal compositions. Use of the combinations of these other insecticides with the compounds of the present invention provide insecticidal compositions which are more effective in controlling insects and often provide results unattainable with separate compositions of the individual insecticides. The other insecticides with which the compounds of this invention can be used in the insecticidal composition to control insects, can include halogenated compounds such as DDT, methoxychlor, TDE, lindane, chlordane, isobenzan, aldrin, dieldrin, heptachlor, endrin, mirex, endosulfon, dicofol and the like; organic phosphorous compounds such as TEPP, schradan, ethion, parathion, methyl parathion, PEN, demeton, carbopheothion, phorate, zinophos, diazinon, malathion, mevinphos, dimethoate, DBD, ronnel, oxydemetonmethyl, dicapthon, chlorothion, phosphamidon, naled, fenthion, trichlorofon, DDVP, and the like; organic nitrogen compound such as dinitro-o-cresol, dinitrocyclohexylphenol, DNB, DNP, binapacril, azobenzene and the like; organic carbamate compounds such as carbaryl, ortho 5353 and the like; organic sulfur compound such as phenothiazine, phenoxathin, lauryl thiocyanate, bis(2-thiocyanoethyl)ether, isobornyl thiocyanoacetate and the like; as well as such substances usually referred to as fumigants, as hydrogen cyanide, carbon tetrachloride, calcium cyanide, carbon disulfide, ethylene dichloride, propylene dichloride, ethylene dibromide, ethylene oxide, methyl bromide, paradichlorobenzene and the like.

The compounds of the present invention can also be combined with fungicidal and nematocidal chemical compounds to form pesticidal compositions useful for the control of fungi and in some cases soil nematodes as well as insects. Typical examples of such fungicidal chemical compounds are ferbam, nabam, zineb, ziram, thiram, chloranil, dichlone, glyodin, cycloheximide, dinocap, maneb, captan, dodine, PNCB, p-dimethylaminobenzenediazo sodium sulfonate and the like; while examples of nematocidal compounds are chloropicrin, 0,0-diehtyl 0-(2,4-dichlorophenyl) phosphorothioate, tetrachlorothiophene, dazomet, dibromochloropropane and the like.

The new compounds of this invention can be used in many ways for the control of insects. Insecticides which are to be used as stomach poisons or protective materials can be applied to the surface on which the insects feed or travel. Insecticides which are to be used as contact poisons or eradicants can be applied directly to the body of the insect, as a residual treatment to the surface on which the insect may walk or crawl, or as a fumigant treatment of the air which the insect breathes. In some cases, the compounds applied to the soil or plant surfaces are taken up by the plant and the insects are poisoned systematically.

The above methods of using insecticides are based on the fact that almost all the injury done by insects is a direct or indirect result of their attempts to secure food. Indeed, the large number of destructive insects can be classified broadly on the basis of their feeding habits. Among the insects which can be effectively controlled by the compounds of the present invention are the chewing insects, such as the Mexican bean bettle and the southern armyworm; the piercing-sucking insects, such as the peach aphid, the cereal leaf bettle, the housefly, the grape leafhopper, the chinch bug, the lygus bug, the oyster shell scale, the California red scale, the Florida red scale, the soft scale and mosquitoes; the internal feeders, including borers, such as the European corn borer, the peach twig borer and the corn earworm, worms or weevils, such as the codling moth, the alfalfa weevil, the cotton boll weevil, the pink boll worm, the plum curculio, the red banded leaf roller, the melonworm, the cabbage looper and the apple maggot, leaf miners such as the apple leaf miner, the birch leaf miner and the beet leaf miner, and gall insects such as the wheat joint worm and the grape phylloxera. Insects which attack below the surface of the ground are classified as subterranean insects and include such destructive pests as the wooly apple aphid, the Japanese beetle, the onion maggot and the corn rootworm.

The quantity of active compound of this invention to be used for insect control will depend on a variety of factors, such as the specific insect involved, intensity of the infestation, weather, type of environment, type of formulation and the like. For example, the application of only one or two ounces of active chemical per acre may be adequate for the control of a light infestation of an insect under conditions unfavorable for its feeding while a pound or more of active compound per acre may be required for the control of a heavy investation of insects under conditions favorable to their development.

The insecticidal activity of the compounds of the present invention was demonstrated by experiments carried out for the control of a variety of insects. In these experiments, the compounds to be tested are first put into a formulation suitable for application at various concentrations and application rates to plants and insects. The desired quantity of the test compound (the quantity being determined by the application concentration or application rate to be used in later testing) is dissolved or dispersed in a solvent consisting of acetone containing 3.19 grams/liter of Triton ®X-155 (alkylaryl polyether alcohol). When it has dissolved or dispersed in the acetone, 4 volumes of the acetone solution or dispersion are diluted with 96 volumes of distilled water. (If the test compound is insoluble in the acetone or distilled water it can be dispersed using a tissue grinder.) Lower concentration test solutions may be made by dilution of higher concentration solutions with a diluent consisting of 96 volumes distilled water and 4 volumes of acetone containing 3.19 grams of Triton ®X-155 per liter.

Test plants used in these experiments are prepared by planting the appropriate seeds in sterilized soil contained in plastic pots having an upper soil surface area of approximately 12.25 square inches (a square pot having a 3.5 inch side). After the seed has been planted, a layer of approximately 0.25 inches of sand is spread on the top surface of the soil. The test compound is applied after the plant has reached a specified size.

For foliar applications, the test compound, dissolved or dispersed in the water/acetone solvent described above, is sprayed as a mist onto the foliage of the test plants. The concentration of the test compound and the total quantity of solution applied is adjusted to give the application concentrations or rates desired. The plants are then allowed to air dry. Mites and aphids are exposed to treated leaves which have been left on the plant. Other insect species are exposed to treated leaves which have been removed from the plant and placed in petri dished containing a piece of moist filter paper.

For soil drench applications, the test compound is first dissolved or dispersed in water/acetone as described above, then the amount of solution required to give a desired application rate is applied, using a pipette, evenly over the top of the soil in the pot. Twenty-four hours after the treatment, mites and aphids are exposed to leaves which have been left on the treated plants. Other insects species are exposed to leaves which have been removed from the plant and placed in petri dishes containing a piece of moist filter paper.

In direct contact applications, the test compound is, again, first formulated into a water/acetone solution, as described above, in the concentrations to be tested. Then the insect to be tested is dipped into, sprayed with or immersed in the liquid, dried and observed for effect.

In the tables below setting forth the experimental data, PPM represents foliar application rates expressed as parts-per-million, #/A represents soil drench application rates expressed as pounds per acre.

CABBAGE LOOPER

Bush lima bean plants (Burpee Variety 222), two-leaf stage, are exposed, at various application rates, to the test compound applied both by the foliar spray and soil drench techniques. Leaves are removed from the plants—after approximately 30 minutes of air-drying for the foliar spray application, after 24 hours for the soil drench application—and placed in petri dishes containing a piece of moist filter paper. Ten cabbage loopers, second instar larval stage, are placed in each petri dish and the dish covered. Observations of insect mortality are made after 48 hours of exposure. Results of these tests are detailed in Table 3 below.

SOUTHERN ARMYWORM

Bush lima bean plants (Burpee Variety 222), two-leaf stage, are exposed, at various application rates, to the test compound applied both by the foliar spray and soil drench techniques. Leaves are removed from the plants—after approximately 30 minutes of air-drying for the foliar spray application, after 24 hours for the soil drench application—and placed in petri dishes containing a piece of moist filter paper. Ten southern armyworms, second instar larval stage, are placed in each petri dish and the dish covered. Observations of insect mortality are made after 48 hours of exposure. Results of these test are detailed in Table 4 below.

SOYBEAN LOOPER

Bush lima bean plants (Burpee Variety 222), two-leaf stage, are exposed, at various application rates, to the test compound applied both by the foliar spray and soil drench techniques. Leaves are removed from the plants—after approximately 30 minutes of air-drying for the foliar spray application, after 24 hours for the soil drench application—and placed in petri dishes containing a piece of moist filter paper. Ten second instar larval soybean loopers are placed in each petri dish and the dish covered. Observations of insect mortality are made after 48 hours of exposure. Results of these test are detailed in Table 5 below.

TOBACCO BUDWORM

Bush lima bean plants (Burpee Variety 222), two-leaf stage, are exposed, at various application rates, to the test compound applied both by the foliar spray and soil drench techniques. Leaves are removed from the plants—after approximately 30 minutes of air-drying for the foliar spray application, after 24 hours for the soil drench application—and placed in petri dishes containing a piece of moist filter paper. Ten tobacco budworms, second instar larval stage, are placed in each petri dish and the dish covered. Observations of insect mortality are made after 48 hours of exposure. Results of these tests are detailed in Table 6 below.

MEXICAN BEAN BETTLE

Bush lima bean plants (Burpee Variety 222), two-leaf stage, are exposed, at various application rates, to the text compound applied both by the foliar spray and soil drench techniques. Leaves are removed from the plants—after approximately 30 minutes of air-drying for the foliar spray application, after 24 hours for the soil drench application—and placed in petri dishes containing a piece of moist filter paper. Ten mexican bean bettles, second instar larval stage, are placed in each petri dish and the dish covered. Observations of insect mortality are made after 48 hours of exposure. Results of these tests are detailed in Table 7 below.

BOLL WEEVIL

Cotton plants (Deltapine 16), two leaf stage, are exposed, at various application rates, to the test compound applied both by the foliar spray and soil drench techniques. Leaves are removed from the plants—after approximately 30 minutes of air-drying for the foliar spray application, after 24 hours for the soil drench application—and placed in petri dishes containing a piece of moist filter paper. Ten adult boll weevils are placed in each petri dish and the dish is then covered. Observations of insect mortality are made after 48 hours of exposure. Results of these tests are detailed in Table 8 below.

GREEN PEACH APHID

Nasturtium plants (Burpee Mixed single Variety 4161) in the 2-3 leaf stage are treated with the test compound, at various application rates, both by the foliar spray and soil drench methods. The plants are air dried for about 30 minutes after the foliar spray is applied, then 25-50 green peach aphids are put on each treated plants and on an untreated control plant by placing an untreated leaf containing 25-50 adult and nymph green peach aphids on the plants. Twenty four hours after a plant has been treated by the soil drench method, it is infestes by 25-50 aphids using the technique described above. An untreated control plant is similarly infested. After 48 hours of exposure of the insects to the treated plants, insect mortality is determined by comparison of the number of insects on the treated plants to the number on the untreated control plant. Results of this testing are set forth in Table 9 below.

PEA APHID

Pea plants (Burpee Wando) in the 10-14 day stage are treated with the test compound, at various application rates, both by foliar spray and soil drench methods. The plants are air dried for about 30 minutes after the foliar spray is applied, then 25-50 pea aphids, adults and nymphs, are put on each treated plant and on an untreated control plant with a small paint brush. Twenty four hours after a plant has been treated by the soil drench method, it is infested by 25-50 aphids using the technique described above. An untreated control plant is similarly infested. After 48 hours of exposure of the insects to the treated plants, insect mortality is determined by comparison of the number of insects on the treated plants to the number on the untreated control plant. Results of this testing are set forth in Table 10 below.

TWO SPOTTED MITE

Bush lima bean plants (Burpee Variety 222) in the two-leaf stage are treated with the test compound, at various application rates, both by the foliar spray and soil drench methods. The plants are air dried for about 30 minutes after the foliar spray is applied, then 50-100 two spotted mites, adults and nymphs, are put on each treated plant and on an untreated control plant by placing an untreated infested bean leaf containing 50-100 mites on the plants. Twenty-four hours after a plant has been treated by the soil drench method, it is infested by 50-100 mites using the technique described above. An untreated control plant is similarly infested. After 48 hours of exposure of the insects to the treated plants, insect mortality is determined by comparison of the number of insects on the treated plants to the number on the untreated control plant. Results of this testing are set forth in Table 11 below.

HOUSEFLY

Ten adult Houseflies are placed in small (2"-3") wire screen cage fitted with a plastic cap. The cage is sprayed with the test compound at the desired concentration in the form of a solution prepared as described hereinabove. After spraying, the treated cages are stored until dry. Sixty minutes after spraying, readings are made of knock down. The cages are then placed on paper toweling moistened with 5-10% sucrose solution and stored on this toweling for 23 hours at which time the 24 hours-after-treatment mortality reading is taken. The results of this test are given in Table 12 below.

GERMAN COCKROACH

Solutions of test compounds are formulated as described hereinbefore and the solution which gives a desired application concentration is placed in a flask. Ten german cockroach adults are placed in a teaspoon tea strainer and are dipped into the test solution. The excess solution is shaken off, the tea strainer opened and the insects placed in a clear plastic container containing a small moist piece of dental wick. The container then is capped with a cover pierced with air holes. Insect mortality is observed 48 hours after the exposure. Results of this testing are indicated in Table 13 below.

SOUTHERN CORN ROOTWORM

A newly germinated corn seed is placed in a one ounce plastic cup fitted with a snap-on plastic lid and covered with approximately 5 grams of sterilized soil. The test compound is formulated into solutions as described hereinbefore and applied to the soil as a soil drench at the desired application rates. After application, the lids are snapped on the cups and the cups are allowed to stand for about 15 minutes to permit the solution to spread evenly through the soil. The lids are then removed, five second instar rootworm larvae are placed on the treated soil and the cups recapped. The cup is examined for insects mortality after 72 hours of exposure. Larvae which cannot crawl or right themselves are considered dead. Results of this testing are given in Table 14 below.

YELLOW FEVER MOSQUITO

Solutions containing the test compound in the desired concentrations are formulated as described hereinabove. Each test solution is placed in a 10 ounce foamed polystyrene cup. Approximately ten 3-4 days old yellow fever mosquito larvae are placed in each test solution with an eyedropper. To each solution is then added a very small pinch of brewer's yeast and a very small piece of dry food (pulverized solid dog chow). Mortality data are taken after 48 hours of exposure. These data are shown in Table 15 below.

The abbreviations used for weed species in tables 1 and 2 are:

| WEED SPECIES | ABBREVIATION |
|---|---|
| Yellow Nutsedge | YNSG |
| Wild Oats | WOAT |
| Jimsonweed | JMWD |
| Velvetleaf | VTLF |
| Johnsongrass | JNGS |
| Pigweed | PIGW |
| Wildmustard | WMSTD |
| Yellow Foxtail | YFLX |
| Barnyardgrass | BNGS |
| Crabgrass | CBGS |
| Cheatgrass | CTGS |
| Wild Morningglory | MNGY |
| Bindweed | BDWD |
| Soybean | SOYB |
| Pinto Beans | PTBN |
| Alfalfa | ALFA |
| Sprangletop | SPGT |
| Oats | OAT |
| Sugar Beet | SUBT |
| Corn | CORN |
| Quackgrass | QKGS |
| Wheat | WHT |
| Cotton | COTN |
| Sorghum | SORG |
| Rice | RICE |

TABLE 1

INJURY RATINGS

WEED SPECIES

| COMPOUND OF EXAMPLE 3: | YNSG | WOAT | JMWD | VTLF | JNGS | PIGW | WMSTD |
|---|---|---|---|---|---|---|---|
| 14 days after treatment, | | | | | | | |
| 8 lbs. per acre application rate | N.E. | 8* | 7* | 4* | 9* | 8* | 6* |
| 4 lbs. per acre application rate | — | — | — | — | — | — | — |
| 2 lbs. per acre application rate | — | 9 | N.E. | 0 | 9 | 5 | 2 |
| 1 lb. per acre application rate | — | 5 | 8 | 0 | 7 | 5 | 0 |
| 0.5 lbs. per acre application rate | — | 0 | 0 | 0 | 6 | 0 | 0 |
| 0.25 lbs. per acre application rate | — | 0 | 0 | 0 | 3 | 2 | 0 |
| 21 days after treatment, | | | | | | | |
| 8 lbs. per acre application rate | 9* | 9* | 9* | 6* | 9* | 9* | 8* |
| 4 lbs. per acre application rate | — | — | — | — | — | — | — |
| 2 lbs. per acre application rate | — | 9 | 9 | 0 | 10 | 2 | 3 |
| 1 lb. per acre application rate | — | 1 | 3 | 0 | 9 | 2 | 2 |
| 0.5 lbs. per acre application rate | — | 0 | 0 | 0 | 7 | 0 | 2 |
| 0.25 lbs. per acre application rate | — | 0 | 0 | 0 | 2 | 1 | 1 |
| COMPOUND OF EXAMPLE 4: | | | | | | | |
| 14 days after treatment, | | | | | | | |
| 8 lbs. per acre application rate | N.E. | 4 | N.E. | 0 | N.E. | 5 | 0 |
| 4 lbs. per acre application rate | 0 | 0 | 0 | 0 | 3 | 0 | 0 |
| 21 days after treatment, | | | | | | | |
| 8 lbs. per acre application rate | N.E. | 0 | N.E. | 0 | N.E. | 3 | 0 |
| 4 lbs. per acre application rate | 2 | 1 | 0 | 0 | 2 | 0 | 1 |

| COMPOUND OF EXAMPLE 3: | YFLX | BNGS | CBGS | CTGS | SPGT | MNGY | BDWD |
|---|---|---|---|---|---|---|---|
| 14 days after treatment, | | | | | | | |
| 8 lbs. per acre application rate | 9* | 9* | 9* | 10* | — | 7* | — |
| 4 lbs. per acre application rate | — | — | — | — | — | — | — |
| 2 lbs. per acre application rate | N.E. | 8 | N.E. | 10 | 8 | 1 | 4 |
| 1 lb. per acre application rate | 7 | 8 | 9 | N.E. | 9 | 1 | 1 |
| 0.5 lb. per acre application rate | 6 | 8 | 8 | 4 | 8 | 2 | 0 |
| 0.25 lb. per acre application rate | 6 | 7 | 6 | 0 | 4 | 1 | 0 |
| 21 days after treatment, | | | | | | | |
| 8 lbs. per acre application rate | 9* | 9* | 9* | 9* | — | 8* | — |
| 4 lbs. per acre application rate | — | — | — | — | — | — | — |
| 2 lbs. per acre application rate | N.E. | 9 | N.E. | N.E. | 9 | 6 | 6 |
| 1 lb. per acre application rate | 7 | 9 | 9 | N.E. | 9 | 0 | 0 |
| 0.5 lbs. per acre application rate | 5 | 7 | 7 | 2 | 6 | 0 | 0 |
| 0.25 lbs. per acre application rate | 6 | 8 | 4 | 0 | 0 | 0 | 0 |
| COMPOUND OF EXAMPLE 4: | | | | | | | |
| 14 days after treatment, | | | | | | | |
| 8 lbs. per acre application rate | N.E. | 8 | 8 | 0 | — | 0 | — |
| 4 lbs. per acre application rate | 1 | 3 | 2 | 0 | — | 0 | — |
| 21 days after treatment, | | | | | | | |
| 8 lbs. per acre application rate | N.E. | 8 | 7 | 0 | — | 0 | — |
| 4 lbs. per acre application rate | 1 | 3 | 0 | 0 | — | 1 | — |

| COMPOUND OF EXAMPLE 3: | SUBT | WHT | RICE | SOYB | COTN | SORG | PTBN |
|---|---|---|---|---|---|---|---|
| 14 days after treatment, | | | | | | | |
| 8 lbs. per acre application rate | — | — | — | — | — | — | — |
| 4 lbs. per acre application rate | — | — | — | — | — | — | — |
| 2 lbs. per acre application rate | 2 | N.E. | 9 | 7 | 1 | 8 | 7 |
| 1 lb. per acre application rate | 1 | 4 | 7 | 7 | 1 | 8 | 4 |
| 0.5 lbs. per acre application rate | 0 | 5 | 4 | 6 | 0 | 7 | 2 |
| 0.25 lbs. per acre application rate | 0 | 1 | 2 | 2 | 0 | 3 | 0 |
| 21 days after treatment, | | | | | | | |
| 8 lbs. per acre application rate | — | — | — | — | — | — | — |

TABLE 1-continued

| | INJURY RATINGS | | | | | | |
|---|---|---|---|---|---|---|---|
| | WEED SPECIES | | | | | | |
| 4 lbs. per acre application rate | — | — | — | — | — | — | — |
| 2 lbs. per acre application rate | 2 | N.E. | 9 | 7 | 0 | 9 | 8 |
| 1 lb. per acre application rate | 1 | 3 | 6 | 7 | 0 | 9 | 6 |
| 0.5 lbs. per acre application rate | 1 | 2 | 3 | 4 | 0 | 8 | 0 |
| 0.25 lbs. per acre application rate | 2 | 1 | 0 | 2 | 0 | 3 | 0 |
| COMPOUND OF EXAMPLE 4: | | | | | | | |
| 14 days after treatment, | | | | | | | |
| 8 lbs. per acre application rate | — | — | — | — | — | — | — |
| 4 lbs. per acre application rate | — | — | — | — | — | — | — |
| 21 days after treatment, | | | | | | | |
| 8 lbs. per acre application rate | — | — | — | — | — | — | — |
| 4 lbs. per acre application rate | — | — | — | — | — | — | — |

| COMPOUND OF EXAMPLE 3: | CORN | QKGS | ALFA | OAT |
|---|---|---|---|---|
| 14 days after treatment, | | | | |
| 8 lbs. per acre application rate | — | — | — | — |
| 4 lbs. per acre application rate | — | — | — | — |
| 2 lbs. per acre application rate | 9 | 9 | 2 | 10 |
| 1 lb. per acre application rate | 9 | 9 | 0 | 6 |
| 0.5 lbs. per acre application rate | 8 | 4 | 0 | 2 |
| 0.25 lbs. per acre application rate | 5 | 3 | 0 | 0 |
| 21 days after treatment, | | | | |
| 8 lbs. per acre application rate | — | — | — | — |
| 4 lbs. per acre application rate | — | — | — | — |
| 2 lbs. per acre application rate | 9 | 10 | 3 | N.E. |
| 1 lb. per acre application rate | 8 | 9 | 0 | 5 |
| 0.5 lbs. per acre application rate | 8 | 4 | 0 | 0 |
| 0.25 lbs. per acre application rate | 5 | 2 | 0 | 0 |
| COMPOUND OF EXAMPLE 4: | | | | |
| 14 days after treatment, | | | | |
| 8 lbs. per acre application rate | — | — | — | — |
| 4 lbs. per acre application rate | — | — | — | — |
| 21 days after treatment, | | | | |
| 8 lbs. per acre application rate | — | — | — | — |
| 4 lbs. per acre application rate | — | — | — | — |

| COMPOUND OF EXAMPLE 5: | YNSG | WOAT | JMWD | VTLF | JNGS | PIGW | WMSTD |
|---|---|---|---|---|---|---|---|
| 14 days after treatment, | | | | | | | |
| 8 lbs. per acre application rate | N.E. | 0 | N.E. | 0 | 0 | N.E. | 0 |
| 21 days after treatment, | | | | | | | |
| 8 lbs. per acre application rate | 0 | 0 | N.E. | 0 | 0 | N.E. | 0 |
| COMPOUND OF EXAMPLE 6: | | | | | | | |
| 14 days after treatment, | | | | | | | |
| 4 lbs. per acre application rate | 9 | 10 | 7 | 4 | 9 | 10 | 5 |
| 2 lbs. per acre application rate | 5* | 5* | 4* | 6* | 8* | 2* | 2* |
| 1 lb. per acre application rate | 1* | 1* | 1* | 0* | 7* | 1* | 3* |
| 0.5 lbs. per acre application rate | — | 1 | 0 | 0 | 7 | 0 | 2 |
| 0.25 lbs. per acre application rate | — | 0 | 0 | 0 | 5 | 0 | 2 |
| 21 days after treatment, | | | | | | | |
| 4 lbs. per acre application rate | 10 | 10 | 7 | 3 | 9 | 10 | 6 |
| 2 lbs. per acre application rate | 3* | 6* | 3* | 0* | 9* | 1* | 2* |
| 1 lb. per acre application rate | 0* | 1* | 0* | 0* | 6* | 0* | 2* |
| 0.5 lbs. per acre application rate | — | 3 | 0 | 0 | 6 | 0 | 7 |
| 0.25 lbs. per acre application rate | — | 2 | 0 | 0 | 4 | 0 | 5 |

| COMPOUND OF EXAMPLE 5: | YFLX | BNGS | CBGS | CTGS | SPGT | MNGY | BDWD |
|---|---|---|---|---|---|---|---|
| 14 days after treatment, | | | | | | | |
| 8 lbs. per acre application rate | N.E. | 0 | 5 | 0 | — | 0 | — |
| 21 days after treatment, | | | | | | | |
| 8 lbs. per acre application rate | 7 | 0 | 0 | 0 | — | 0 | — |
| COMPOUND OF EXAMPLE 6: | | | | | | | |
| 14 days after treatment, | | | | | | | |
| 4 lbs. per acre application rate | 10 | 10 | 9 | N.E. | — | 8 | — |
| 2 lbs. per acre application rate | 7* | 9* | 7* | 9* | 10 | 3* | 6 |
| 1 lb. per acre application rate | 6* | 9* | 6* | 4* | 10 | 3* | 3 |
| 0.5 lbs. per acre application rate | 6 | 8 | 9 | 5 | 9 | 4 | 1 |
| 0.25 lbs. per acre application rate | 4 | 7 | 9 | 3 | 5 | 3 | 1 |
| 21 days after treatment, | | | | | | | |
| 4 lbs. per acre application rate | 9 | 10 | 9 | 10 | — | 9 | — |
| 2 lbs. per acre application rate | 7* | 10* | 7* | 7* | 10 | 3* | 7 |
| 1 lb. per acre application rate | 5* | 9* | 6* | 4* | 10 | 2* | 4 |
| 0.5 lbs. per acre application rate | 6 | 8 | 7 | 4 | 9 | 6 | 3 |
| 0.25 lbs. per acre application rate | 5 | 8 | 7 | 2 | 4 | 4 | 2 |

| COMPOUND OF EXAMPLE 5: | SUBT | WHT | RICE | SOYB | COTN | SORG | PTBN |
|---|---|---|---|---|---|---|---|
| 14 days after treatment, | | | | | | | |
| 8 lbs. per acre application rate | — | — | — | — | — | — | — |
| 21 days after treatment, | | | | | | | |
| 8 lbs. per acre application rate | — | — | — | — | — | — | — |

TABLE 1-continued
INJURY RATINGS
WEED SPECIES

| COMPOUND OF EXAMPLE 6: | | | | | | | |
|---|---|---|---|---|---|---|---|
| 14 days after treatment, | — | — | — | — | — | — | — |
| 4 lbs. per acre application rate | — | — | — | — | — | — | — |
| 2 lbs. per acre application rate | 2 | 9 | N.E. | 8 | 1 | 9 | 7 |
| 1 lb. per acre application rate | 1 | 9 | 10 | 8 | 1 | 9 | 6 |
| 0.5 lbs. per acre application rate | 0 | 8 | 7 | 6 | 0 | 9 | 0 |
| 0.25 lbs. per acre application rate | 0 | 7 | 3 | 1 | 0 | 5 | 0 |
| 21 days after treatment, | | | | | | | |
| 4 lbs. per acre application rate | — | — | — | — | — | — | — |
| 2 lbs. per acre application rate | 1 | 10 | 10 | 8 | 1 | 10 | 7 |
| 1 lb. per acre application rate | 2 | 9 | 9 | 8 | 1 | 10 | 6 |
| 0.5 lbs. per acre application rate | 2 | 8 | 6 | 6 | 0 | 9 | 0 |
| 0.25 lbs. per acre application rate | 0 | 7 | 1 | 0 | 0 | 3 | 0 |

| COMPOUND OF EXAMPLE 5: | CORN | QKGS | ALFA | OAT |
|---|---|---|---|---|
| 14 days after treatment, | | | | |
| 8 lbs. per acre application rate | — | — | — | — |
| 21 days after treatment, | | | | |
| 8 lbs. per acre application rate | — | — | — | — |
| COMPOUND OF EXAMPLE 6: | | | | |
| 14 days after treatment, | | | | |
| 4 lbs. per acre application rate | — | — | — | — |
| 2 lbs. per acre application rate | 8 | 9 | 2 | 9 |
| 1 lb. per acre application rate | 8 | 7 | 2 | 3 |
| 0.5 lbs. per acre application rate | 7 | 6 | 2 | 2 |
| 0.25 lbs. per acre application rate | 2 | 3 | 1 | 0 |
| 21 days after treatment, | | | | |
| 4 lbs. per acre application rate | — | — | — | — |
| 2 lbs. per acre application rate | 9 | 10 | 1 | 10 |
| 1 lb. per acre application rate | 9 | 7 | 1 | 3 |
| 0.5 lbs. per acre application rate | 8 | 8 | 2 | 2 |
| 0.25 lbs. per acre application rate | 3 | 3 | 0 | 0 |

| COMPOUND OF EXAMPLE 7: | YNGS | WOAT | JMWD | VTLF | JNGS | PIGW | WMSTD |
|---|---|---|---|---|---|---|---|
| 14 days after treatment, | | | | | | | |
| 8 lbs. per acre application rate | N.E. | 9 | N.E. | 5 | 9 | 2 | 0 |
| 4 lbs. per acre application rate | — | — | — | — | — | — | — |
| 2 lbs. per acre application rate | 9 | 4 | 0 | 4 | 9 | 0 | 0 |
| 1 lb. per acre application rate | 0 | 0 | 0 | 1 | 9 | 0 | 0 |
| 21 days after treatment, | | | | | | | |
| 8 lbs. per acre application rate | 8 | 9 | N.E. | 6 | 9 | 0 | 2 |
| 4 lbs. per acre application rate | — | — | — | — | — | — | — |
| 2 lbs. per acre application rate | 6 | 3 | 0 | 5 | 9 | 0 | 0 |
| 1 lb. per acre application rate | 2 | 0 | 0 | 2 | 7 | 0 | 0 |
| COMPOUND OF EXAMPLE 13 | | | | | | | |
| 14 days after treatment, | | | | | | | |
| 8 lbs. per acre application rate | 0 | 0 | 0 | 0 | 0 | 0 | 0 |
| 4 lbs. per acre application rate | — | — | — | — | — | — | — |
| 2 lbs. per acre application rate | 0 | 0 | 2 | 0 | N.E. | 0 | 0 |
| 1 lb. per acre application rate | 0 | 0 | 0 | 0 | 0 | 0 | 0 |
| 21 days after treatment, | | | | | | | |
| 8 lbs. per acre application rate | 0 | 0 | 0 | 0 | 7 | 0 | 0 |
| 4 lbs. per acre application rate | — | — | — | — | — | — | — |
| 2 lbs. per acre application rate | 0 | 0 | 0 | 0 | 0 | 1 | 0 |

| COMPOUND OF EXAMPLE 7: | YFLX | BNGS | CBGS | SPGT | CTGS | MNGY | BDWD |
|---|---|---|---|---|---|---|---|
| 14 days after treatment | | | | | | | |
| 8 lbs. per acre application rate | 9 | 10 | 9 | — | N.E. | 0 | — |
| 4 lbs. per acre application rate | — | — | — | — | — | — | — |
| 2 lbs. per acre application rate | 7 | 10 | 9 | — | 9 | 1 | — |
| 1 lb. per acre application rate | 6 | 9 | 6 | — | 7 | 0 | — |
| 21 days after treatment, | | | | | | | |
| 8 lbs. per acre application rate | 9 | 9 | 9 | — | N.E. | 0 | — |
| 4 lbs. per acre application rate | — | — | — | — | — | — | — |
| 2 lbs. per acre application rate | 7 | 10 | 7 | — | 9 | 0 | — |
| 1 lb. per acre application rate | 5 | 8 | 4 | — | 6 | 0 | — |
| COMPOUND OF EXAMPLE 13: | | | | | | | |
| 14 days after treatment. | | | | | | | |
| 8 lbs. per acre application rate | 0 | 0 | 0 | — | 2 | 0 | — |
| 4 lbs. per acre application rate | — | — | — | — | — | — | — |
| 2 lbs. per acre application rate | 0 | 0 | 0 | — | 0 | 2 | — |
| 1 lb. per acre application rate | 0 | 0 | 0 | — | 0 | 0 | — |
| 21 days after treatment, | | | | | | | |
| 8 lbs. per acre application rate | 0 | 0 | 0 | — | 0 | 2 | 0 |
| 4 lbs. per acre application rate | — | — | — | — | — | — | — |
| 2 lbs. per acre application rate | 0 | 0 | 0 | — | 0 | 2 | — |
| 1 lb. per acre application rate | 0 | 0 | 0 | — | 0 | 2 | — |

| COMPOUND OF EXAMPLE 7: | SUBT | WHT | SOYB | COTN | SORG | PTBN |
|---|---|---|---|---|---|---|

TABLE 1-continued

INJURY RATINGS
WEED SPECIES

| | | | | | | |
|---|---|---|---|---|---|---|
| 14 days after treatment, | | | | | | |
| 8 lbs. per application rate | — | — | — | — | — | — |
| 8 lbs. per acre application rate | — | — | — | — | — | — |
| 4 lbs. per acre application rate | — | — | — | — | — | — |
| 2 lbs. per acre application rate | — | — | — | — | — | — |
| 1 lb. per acre application rate | — | — | — | — | — | — |
| 21 days after treatment, | | | | | | |
| 8 lbs. per acre application rate | — | — | — | — | — | — |
| 4 lbs. per acre application rate | — | — | — | — | — | — |
| 2 lbs. per acre application rate | — | — | — | — | — | — |
| 1 lb. per acre application rate | — | — | — | — | — | — |
| COMPOUND OF EXAMPLE 13: | | | | | | |
| 14 days after treatment, | | | | | | |
| 8 lbs. per acre application rate | — | — | — | — | — | — |
| 4 lbs. per acre application rate | — | — | — | — | — | — |
| 2 lbs. per acre application rate | — | — | — | — | — | — |
| 1 lb. per acre application rate | — | — | — | — | — | — |
| 21 days after treatment, | | | | | | |
| 8 lbs. per acre application rate | — | — | — | — | — | — |
| 4 lbs. per acre application rate | — | — | — | — | — | — |
| 2 lbs. per acre application rate | — | — | — | — | — | — |
| 1 lb. per acre application rate | — | — | — | — | — | — |

| COMPOUND OF EXAMPLE 7: | CORN | QKGS | ALFA | OAT |
|---|---|---|---|---|
| 14 days after treatment, | | | | |
| 8 lbs. per applicaton rate | — | — | — | — |
| 4 lbs. per acre application rate | — | — | — | — |
| 2 lbs. per acre application rate | — | — | — | — |
| 2 lbs. per acre application rate | — | — | — | — |
| 1 lb. per acre application rate | — | — | — | — |
| 21 days after treatment, | | | | |
| 8 lbs. per acre application rate | — | — | — | — |
| 4 lbs. per acre application rate | — | — | — | — |
| 2 lbs. per acre application rate | — | — | — | — |
| 1 lb. per acre application rate | — | — | — | — |
| COMPOUND OF EXAMPLE 13: | | | | |
| 14 days after treatment, | | | | |
| 8 lbs. per acre application rate | — | — | — | — |
| 4 lbs. per acre application rate | — | — | — | — |
| 2 lbs. per acre application rate | — | — | — | — |
| 1 lb. per acre application rate | — | — | — | — |
| 21 days after treatment, | | | | |
| 8 lbs. per acre application rate | — | — | — | — |
| 4 lbs. per acre application rate | — | — | — | — |
| 2 lbs. per acre application rate | — | — | — | — |
| 1 lb. per acre application rate | — | — | — | — |

* = Average of two or more replicates

TABLE 2

INJURY RATINGS
WEED SPECIES

| COMPOUND OF EXAMPLE 3: | WMSTD | WOAT | BDWD | BNGS | SOYB | CBGS | YLFX |
|---|---|---|---|---|---|---|---|
| 14 days after treatment, | | | | | | | |
| 8 lbs. per acre application rate | 10 | 7 | 6 | 8 | 10 | 8 | 8 |
| COMPOUND OF EXAMPLE 4: | | | | | | | |
| 14 days after treatment, | | | | | | | |
| 8 lbs. per acre application rate | 3 | 0 | 2 | 0 | 0 | 4 | 1 |
| COMPOUND OF EXAMPLE 6: | | | | | | | |
| 14 days after treatment, | | | | | | | |
| 2 lbs. per acre application rate | 4* | 2* | 3* | 7* | 8* | 7* | 7* |
| 1 lb. per acre application rate | 3* | 0* | 4* | 7* | 8* | 6* | 6* |
| 0.5 lbs. per acre application rate | 1.5* | 0* | 1.5* | 4* | 5* | 4* | 2* |
| 0.25 lbs. per acre application rate | 0* | 0* | *0* | 3* | 1.5* | 1* | 0* |

| COMPOUND OF EXAMPLE 3: | JNGS | MNGY | JMWD | YNGS | CTGS | PIGW | SUBT |
|---|---|---|---|---|---|---|---|
| 14 days after treatment, | | | | | | | |
| 8 lbs. per acre application rate | 6 | 8 | 7 | 8 | 5 | — | — |
| COMPOUND OF EXAMPLE 4: | | | | | | | |
| 14 days after treatment, | | | | | | | |
| 8 lbs. per acre application rate | 0 | 0 | 0 | 0 | 4 | — | — |
| COMPOUND OF EXAMPLE 6: | | | | | | | |
| 14 days after treatment, | | | | | | | |
| 2 lbs. per acre application rate | 7* | 7* | 4* | 4* | 2* | 1* | 3* |
| 1 lb. per acre application rate | 7* | 7* | 3* | 3* | 1* | 1* | 0* |
| 0.5 lbs. per acre application rate | 6* | 4* | 3* | 0* | 0* | 1* | 0 |

TABLE 2-continued
INJURY RATINGS
WEED SPECIES

| | | | | | | | |
|---|---|---|---|---|---|---|---|
| 0.25 lbs. per acre application rate | 4* | 3* | 1.5* | 0* | 0* | 0* | 1* |
| COMPOUND OF EXAMPLE 3: | SORG | WHT | RICE | COTN | VTLF | QKGS | CORN |
| 14 days after treatment, 8 lbs. per acre application rate | — | — | — | — | — | — | — |
| COMPOUND OF EXAMPLE 4: | | | | | | | |
| 14 days after treatment, 8 lbs. per acre application rate | — | — | — | — | — | — | — |
| COMPOUND OF EXAMPLE 6: | | | | | | | |
| 14 days after treatment, 2 lbs. per acre application rate | 4* | 4* | 4* | 4* | 3* | 5* | 6* |
| 1 lb. per acre application rate | 2* | 4* | 4* | 3* | 1* | 3* | 6* |
| 0.5 lbs. per acre application rate | 1* | 0* | 2* | 1* | 0* | 3* | 4* |
| 0.25 lbs. per acre application rate | 1* | 0* | 1* | 3* | 1* | 2* | 2* |
| COMPOUND OF EXAMPLE 3: | PTBN | ALFA | OAT | SPTG | | | |
| 14 days after treatment, 8 lbs. per acre application rate | — | — | — | — | | | |
| COMPOUND OF EXAMPLE 4: | | | | | | | |
| 14 days after treatment, 2 lbs. per acre application rate | — | — | — | | | | |
| 1 lb. per acre application rate | | | | | | | |
| COMPOUND OF EXAMPLE 6: | | | | | | | |
| 14 days after treatment, 2 lbs. per acre application | 3* | 2* | 3* | 5* | | | |
| 1 lb. per acre application | 1* | 1* | 1* | 6* | | | |
| 0.5 lbs. per acre application | 1* | 0* | 1* | 4* | | | |
| 0.25 lbs. per acre application | 1* | 0* | 0* | 2* | | | |
| COMPOUND OF EXAMPLE 7: | WMSTD | WOAT | BDWD | BNGS | SOYB | CBGS | YLFX |
| 14 days after treatment, 8 lbs. per acre application rate | 10 | 8 | 4 | 9 | 9 | 8 | 8 |
| 2 lbs. per acre application rate | 3* | 1* | 1* | 7* | 6* | 6* | 7* |
| 1 lb. per acre application rate | 2* | 1* | 1* | 7* | 6* | 6* | 4* |
| 0.5 lbs. per acre application rate | 0 | 0 | 1 | 6 | 3 | 3 | 2 |
| 0.25 lbs. per acre application rate | 0 | 0 | 0 | 2 | 4 | 2 | 2 |
| COMPOUND OF EXAMPLE 10: | | | | | | | |
| 14 days after treatment, 8 lbs. per acre application rate | 2 | 7 | 0 | 8 | 5 | 8 | 9 |
| COMPOUND OF EXAMPLE 13: | | | | | | | |
| 14 days after treatment, 8 lbs. per acre application rate | 0 | 1 | 0 | 1 | 4 | 0 | 3 |
| 2 lbs. per acre application rate | 0 | 2 | 0 | 0 | 2 | 0 | 2 |
| 1 lb. per acre application rate | 0 | 0 | 0 | 0 | 1 | 0 | 0 |
| COMPOUND OF EXAMPLE 7: | JNGS | MNGY | JMWD | YNSG | CTGS | PIGW | SUBT |
| 14 days after after treatment 8 lbs. per acre application rate | 9 | 7 | 6 | 8 | — | 0 | — |
| 2 lbs. per acre application rate | 8* | 4* | 2* | 1 | 1 | 2* | 2* |
| 1 lb. per acre application rate | 6 | 2 | 3 | — | 0 | 0 | 0 |
| 0.5 lbs. per acre application rate | 6 | 2 | 3 | — | 0 | 0 | 0 |
| 0.25 lbs. per acre application rate | 4 | 2 | 0 | — | 0 | 0 | 0 |
| COMPOUND OF EXAMPLE 10: | | | | | | | |
| 14 days after treatment, 8 lbs. per acre application rate | 7 | 7 | 0 | 6 | — | 2 | — |
| COMPOUND OF EXAMPLE 13: | | | | | | | |
| 14 days after treatment, 8 lbs. per acre application rate | 4 | 0 | 0 | 0 | — | 0 | — |
| 2 lbs. per acre application rate | 0 | 0 | 0 | 0 | — | 0 | — |
| 1 lb. per acre application rate | 2 | 0 | 0 | 2 | — | 0 | — |
| COMPOUND OF EXAMPLE 7: | SORG | WHT | RICE | COTN | VTLF | QKGS | CORN |
| 14 days after treatment, 8 lbs. per acre application rate | — | — | — | — | — | — | — |
| 2 lbs. per acre application rate | 4 | 5 | 6 | 7 | 2 | 4 | 7 |
| 1 lb. per acre application rate | 3 | 0 | 6 | 6 | 2 | 2 | 6 |
| 0.5 lbs. per acre application rate | 3 | 0 | 6 | 3 | 2 | 3 | 4 |
| 0.25 lbs. per acre application rate | 2 | 0 | 0 | 3 | 0 | 0 | 3 |
| COMPOUND OF EXAMPLE 10: | | | | | | | |
| 14 days after treatment, 8 lbs. per acre application rate | — | — | — | — | — | — | — |
| COMPOUND OF EXAMPLE 13: | | | | | | | |
| 14 days after treatment, 8 lbs. per acre application rate | — | — | — | — | — | — | — |
| 2 lbs. per acre application rate | — | — | — | — | — | — | — |
| 1 lb. per acre application rate | — | — | — | — | — | — | — |

TABLE 2-continued

INJURY RATINGS

| COMPOUND OF EXAMPLE 7: | PTBN | ALFA | OAT | SPGT |
|---|---|---|---|---|
| 14 days after treatment, | | | | |
| 8 lbs. per acre application rate | — | — | — | — |
| 2 lbs. per acre application rate | 5 | 2 | 0 | 6 |
| 1 lb. per acre application rate | 3 | 1 | 0 | 4 |
| 0.5 lbs. per acre application rate | 2 | 0 | 0 | 0 |
| 0.25 lbs. per acre application rate | 2 | 0 | 0 | 0 |
| COMPOUND OF EXAMPLE 10: | | | | |
| 14 days after treatment, | | | | |
| 8 lbs. per acre application rate | — | — | — | — |
| COMPOUND OF EXAMPLE 13: | | | | |
| 14 days after treatment, | | | | |
| 8 lbs. per acre application rate | — | — | — | — |
| 2 lbs. per acre application rate | — | — | — | — |
| 1 lb. per acre application rate | — | — | — | — |

NOTE:
* = Average of two or more replicates

TABLE 3

PERCENT CONTROL

| TEST COMPOUND | APPLICATION RATE PPM or #/A | 1024 | 512 | 256 | 128 | 64 | 32 |
|---|---|---|---|---|---|---|---|
| COMPOUND OF EXAMPLE 3: | PPM | 20 | 10 | 0 | 0 | 0 | 0 |
|  | #/A | — | — | — | — | — | — |
| COMPOUND OF EXAMPLE 4: | PPM | 0 | 0 | 0 | 0 | 0 | 0 |
|  | #/A | — | — | — | — | — | — |
| COMPOUND OF EXAMPLE 5: | PPM | 0 | 0 | 0 | 0 | 0 | 0 |
|  | #/A | — | — | — | — | — | — |
| COMPOUND OF EXAMPLE 6: | PPM | 100 | 100 | 100 | 80 | 0 | — |
|  | #/A | — | — | — | — | 0 | — |
| COMPOUND OF EXAMPLE 12: | PPM | 40 | 40 | 20 | 0 | 0 | — |
|  | #/A | — | — | — | — | 0 | — |

TABLE 4

PERCENT CONTROL

| TEST COMPOUND | APPLICATION RATE PPM or #1A | 1024 | 512 | 256 | 128 | 64 | 32 | 16 | 8 |
|---|---|---|---|---|---|---|---|---|---|
| COMPOUND OF EXAMPLE 3: | PPM | 10 | 20 | 10 | 0 | 0 | 0 | — | — |
|  | #/A | 50 | — | — | — | — | — | — | — |
| COMPOUND OF EXAMPLE 4: | PPM | 90 | 80 | 50 | 30 | 30 | 10 | — | — |
|  | #/A | 10 | — | — | — | — | — | — | — |
| COMPOUND OF EXAMPLE 5: | PPM | 40 | 30 | 20 | 10 | 10 | 0 | — | — |
|  | #/A | 20 | — | — | — | — | — | — | — |
| COMPOUND OF EXAMPLE 6: | PPM | 100 | 100 | 100 | 100 | 100* | 90 | 50 | 0 |
|  | #/A | — | — | — | — | 20 | — | — | — |
| COMPOUND OF EXAMPLE 10: | PPM | 100 | 100 | 80 | 88 | 64 | — | — | — |
|  | #/A | — | — | — | — | 40 | 0 | 0 | 0 |
| COMPOUND OF EXAMPLE 12: | PPM | 100 | 70 | 20 | 0 | 0 | — | — | — |
|  | #/A | — | — | — | — | — | — | — | — |

Note:
* = Average of two replicates

TABLE 5

PERCENT CONTROL

| TEST COMPOUND | APPLICATION RATE PPM or #/A | 1024 | 512 | 256 | 128 | 64 | 32 | 16 | 8 |
|---|---|---|---|---|---|---|---|---|---|
| COMPOUND OF EXAMPLE 6: | PPM | 90 | 100 | 100 | 90 | 90* | 30 | 20 | 0 |
|  | #/A | — | — | — | — | — | — | — | — |
| COMPOUND OF EXAMPLE 12: | PPM | 100 | 100 | 100 | 80 | 10 | — | — | — |
|  | #/A | — | — | — | — | 20 | — | — | — |

NOTE:
* = Average of two replicates

TABLE 6

PERCENT CONTROL

| TEST COMPOUND | APPLICATION RATE PPM or #/A | 1024 | 512 | 256 | 128 | 64 |
|---|---|---|---|---|---|---|
| COMPOUND OF EXAMPLE 6 | PPM | 90 | 40 | 10 | 20 | 10 |

TABLE 6-continued

| TEST COMPOUND | APPLICATION RATE PPM or #/A | PERCENT CONTROL | | | | |
|---|---|---|---|---|---|---|
| | | 1024 | 512 | 256 | 128 | 64 |
| | #/A | — | — | — | — | 0 |
| COMPOUND OF EXAMPLE 12: | PPM | 40 | — | — | — | — |
| | #/A | — | — | — | — | 0 |

TABLE 7

| TEST COMPOUND | APPLICATION RATE PPM or #/A | PERCENT CONTROL | | | | | | | | |
|---|---|---|---|---|---|---|---|---|---|---|
| | | 1024 | 512 | 256 | 128 | 64 | 32 | 16 | 8 | 4 |
| COMPOUND OF EXAMPLE 3: | PPM | 100 | 100 | 100 | 50 | 20 | 20 | — | — | — |
| | #/A | 100 | — | — | — | — | 90 | 40 | 30 | 10 |
| COMPOUND OF EXAMPLE 4: | PPM | 100 | 100 | 80 | 40 | 0 | 0 | — | — | — |
| | #/A | 70 | — | — | — | — | — | — | — | — |
| COMPOUND OF EXAMPLE 5: | PPM | 60 | 20 | 0 | 0 | 0 | 0 | — | — | — |
| | #/A | 10 | — | — | — | — | — | — | — | — |
| COMPOUND OF EXAMPLE 6: | PPM | 100 | 100 | 100 | 90 | 90* | 60 | 30 | 50 | — |
| | #/A | — | — | — | — | 60 | — | — | — | — |
| COMPOUND OF EXAMPLE 10: | PPM | 90 | 30 | 20 | 20 | 10 | — | — | — | — |
| | #/A | — | — | — | — | 20 | 0 | 10 | 0 | — |
| COMPOUND OF EXAMPLE 12: | PPM | 100 | 60 | 20 | 0 | 0 | — | — | — | — |
| | #/A | — | — | — | — | 20 | — | — | — | — |

NOTE:
* = Average of two replicates

TABLE 8

| TEST COMPOUND | APPLICATION RATE PPM or #/A | PERCENT CONTROL | | | | | | | |
|---|---|---|---|---|---|---|---|---|---|
| | | 1024 | 512 | 256 | 128 | 64 | 32 | 16 | 8 |
| COMPOUND OF EXAMPLE 3: | PPM | 30 | 0 | 0 | 0 | 0 | 0 | — | — |
| | #/A | 0 | — | — | — | — | — | — | — |
| COMPOUND OF EXAMPLE 4: | PPM | 20 | 20 | 10 | 10 | 0 | 0 | — | — |
| | #/A | 10 | — | — | — | — | — | — | — |
| COMPOUND OF EXAMPLE 5: | PPM | 20 | 10 | 0 | 0 | 0 | 0 | — | — |
| | #/A | 10 | — | — | — | — | — | — | — |
| COMPOUND OF EXAMPLE 6: | PPM | 50 | — | — | — | — | — | — | — |
| | #/A | — | — | — | — | 0 | — | — | — |
| COMPOUND OF EXAMPLE 10: | PPM | 0 | 0 | 0 | 10 | 0 | — | — | — |
| | #/A | — | — | — | — | 0 | 10 | 0 | 0 |
| COMPOUND OF EXAMPLE 12: | PPM | 50 | — | — | — | — | — | — | — |
| | #/A | — | — | — | — | 0 | — | — | — |

TABLE 9

| TEST COMPOUND | APPLICATION RATE PPM or #/A | PERCENT CONTROL | | | | | | | | |
|---|---|---|---|---|---|---|---|---|---|---|
| | | 1024 | 512 | 256 | 128 | 64 | 32 | 16 | 8 | 4 |
| COMPOUND OF EXAMPLE 3: | PPM | 85 | 70 | 60 | 40 | 20 | 0 | — | — | — |
| | #/A | 90 | — | — | — | — | 66 | 50 | 50 | 0 |
| COMPOUND OF EXAMPLE 4: | PPM | 100 | 90 | 90 | 70 | 70 | 40 | — | — | — |
| | #/A | 100 | — | — | — | — | 100 | 90 | 70 | 50 |
| COMPOUND OF EXAMPLE 5: | PPM | 100 | 90 | 75 | 60 | 50 | 40 | — | — | — |
| | #/A | 100 | — | — | — | — | 100 | 100 | 90 | 86 |
| COMPOUND OF EXAMPLE 6: | PPM | 90 | 100 | 100 | 100 | 100, 90 | 0 | 0 | 0 | — |
| | #/A | — | — | — | — | 100 | 70 | 70 | 69 | — |
| COMPOUND OF EXAMPLE 10: | PPM | 95 | 100 | 90 | 85 | 90 | 75 | 50 | 0 | 0 |
| | #/A | — | — | — | — | 100 | 100 | 100 | 80 | — |
| COMPOUND OF EXAMPLE 12: | PPM | 90 | 50 | 0 | 0 | 0 | — | — | — | — |
| | #/A | — | — | — | — | 55 | — | — | — | — |

TABLE 10

| TEST COMPOUND | APPLICATION RATE PPM or #/A | PERCENT CONTROL | | | | | | | | | | |
|---|---|---|---|---|---|---|---|---|---|---|---|---|
| | | 1024 | 512 | 256 | 128 | 64 | 32 | 16 | 8 | 4 | 2 | 1 |
| COMPOUND OF EXAMPLE 3: | PPM | 100 | 100 | 100 | 100 | 100 | 80 | — | — | — | — | — |
| | #/A | 100 | — | — | — | — | 100 | 100 | 100 | 90 | — | — |
| COMPOUND OF EXAMPLE 4: | PPM | 100 | 100 | 100 | 100 | 90 | 70 | — | — | — | — | — |
| | #/A | 100 | — | — | — | — | 100 | 100 | 100 | 100 | — | — |
| COMPOUND OF EXAMPLE 5: | PPM | 100 | 90 | 80 | 75 | 75 | 70 | — | — | — | — | — |
| | #/A | 100 | — | — | — | — | 100 | 100 | 100 | 50 | — | — |
| COMPOUND OF EXAMPLE 6: | PPM | 100 | 100 | 98 | 80 | 80 | — | — | — | — | — | — |

TABLE 10-continued

| TEST COMPOUND | APPLICATION RATE PPM or #/A | PERCENT CONTROL | | | | | | | | | |
|---|---|---|---|---|---|---|---|---|---|---|---|
| | | 1024 | 512 | 256 | 128 | 64 | 32 | 16 | 8 | 4 | 2 | 1 |
| | #/A | — | — | — | — | 100 | 100 | 100 | 100 | 80 | 72 | 79 |
| COMPOUND OF EXAMPLE 10: | PPM | 100 | 100 | 100 | 100 | 90 | 25 | 0 | 0 | 0 | — | — |
| | #/A | — | — | — | — | 100 | 80 | 60 | 10 | — | — | — |
| COMPOUND OF EXAMPLE 12: | PPM | 100 | 80 | 80 | 0 | 0 | — | — | — | — | — | — |
| | #/A | — | — | — | — | 100 | 100 | 100 | 100 20 | 0 | 0 | |

TABLE 11

| TEST COMPOUND | APPLICATION RATE PPM or #/A | PERCENT CONTROL | | | | | | | | |
|---|---|---|---|---|---|---|---|---|---|---|
| | | 1024 | 512 | 256 | 128 | 64 | 32 | 16 | 8 | 4 |
| COMPOUND OF EXAMPLE 3: | PPM | 94 | 88 | 84 | 80 | 60 | 50 | — | — | — |
| | #/A | 95 | 90 | 85 | — | — | 40 | 40 | 0 | 0 |
| COMPOUND OF EXAMPLE 4: | PPM | 85 | 80 | 80 | 80 | 60 | 0 | — | — | — |
| | #/A | — | — | — | — | — | — | — | — | — |
| COMPOUND OF EXAMPLE 5: | PPM | 90 | 90 | 90 | 85 | 80 | 75 | — | — | — |
| | #/A | — | — | — | — | — | — | — | — | — |
| COMPOUND OF EXAMPLE 6: | PPM | 100 | 100 | 100 | 100 | 50 | — | — | — | — |
| | #/A | — | — | — | — | 0 | — | — | — | — |
| COMPOUND OF EXAMPLE 10: | PPM | 98 | 94 | 98 | 98 | 60 | — | — | — | — |
| | #/A | — | — | — | — | 70 | 60 | 72 | 10 | — |
| COMPOUND OF EXAMPLE 12: | PPM | 100 | 70 | 0 | 0 | 0 | — | — | — | — |
| | #/A | — | — | — | — | 80 | — | — | — | — |

TABLE 12

| TEST COMPOUND | RATE, PPM | PERCENT CONTROL | | | | | | | |
|---|---|---|---|---|---|---|---|---|---|
| | | 1024 | 512 | 256 | 128 | 64 | 32 | 16 | 8 |
| COMPOUND OF EXAMPLE 3: | k | 70 | 60 | 30 | 0 | 0 | 0 | — | — |
| | m | 100 | 90 | 70 | 0 | 0 | 0 | — | — |
| COMPOUND OF EXAMPLE 4: | k | 90 | 40 | 30 | 30 | 0 | 0 | — | — |
| | m | 100 | 60 | 40 | 10 | 10 | 10 | — | — |
| COMPOUND OF EXAMPLE 5: | k | 30 | 0 | 0 | 0 | 0 | 0 | — | — |
| | m | 40 | 0 | 0 | 0 | 0 | 0 | — | — |
| COMPOUND OF EXAMPLE 6: | k | 90 | 100 | 100 | 90 | 100* | 100 | 100 | 100 |
| | m | 100 | 100 | 100 | 100 | 100* | 100 | 90 | 60 |
| COMPOUND OF EXAMPLE 10: | k | 100 | 80 | 0 | 0 | 0 | — | — | — |
| | m | 100 | 100 | 100 | 60 | 80 | — | — | — |
| COMPOUND OF EXAMPLE 12: | k | 100 | 100 | 100 | 90 | 80* | 100 | 100 | 100 |
| | m | 100 | 100 | 100 | 100 | 95* | 90 | 70 | 80 |

NOTE:
k = 60 Minute Knockdown
m = 24 Hour Mortality
* = Average of Two Replicates

TABLE 13

| TEST COMPOUND | APPLICATION RATE, PPM | PERCENT CONTROL | | | | | |
|---|---|---|---|---|---|---|---|
| | | 1024 | 512 | 256 | 128 | 64 | 32 | 16 |
| COMPOUND OF EXAMPLE 6: | | 100 | 100 | 40 | 0 | 20 | — | — |
| COMPOUND OF EXAMPLE 10: | | 100 | 90 | 10 | 0 | 10 | 0 | — |
| COMPOUND OF EXAMPLE 12: | | 90 | 40 | 10 | 20 | 10 | — | — |

TABLE 14

| TEST COMPOUND | APPLICATION RATE, #/A | PERCENT CONTROL | | | | | | |
|---|---|---|---|---|---|---|---|---|
| | | 64 | 32 | 8 | 4 | 2 | 1 | 0.5 | 0.25 |
| COMPOUND OF EXAMPLE 3: | | — | — | 100 | 100 | 80 | 80 | 60 | 20 |
| COMPOUND OF EXAMPLE 4: | | — | — | 100 | 100 | 80 | 40 | 40 | 20 |
| COMPOUND OF EXAMPLE 5: | | — | — | 80 | 20 | 20 | 10 | 20 | 10 |
| COMPOUND OF EXAMPLE 6: | | 100 | 100 | 0 | 0 | — | — | — | — |
| COMPOUND OF EXAMPLE 12: | | 80 | — | — | — | — | — | — | — |

TABLE 15

| TEST COMPOUND | APPLICATION RATE, PPM | PERCENT CONTROL | | | |
|---|---|---|---|---|---|
| | | 10.0 | 1.0 | 0.1 | 0.01 |
| COMPOUND OF EXAMPLE 3: | | 100 | 80 | 30 | 20 |
| COMPOUND OF EXAMPLE 4: | | 100 | 100 | 80 | 70 |
| COMPOUND OF EXAMPLE 5: | | 100 | 100 | 90 | 70 |
| COMPOUND OF EXAMPLE 6: | | 100 | 90 | 40 | 20 |
| COMPOUND OF EXAMPLE 10: | | 100 | 80 | 60 | 40 |
| COMPOUND OF EXAMPLE 12: | | 100 | 90 | 70 | 40 |

I claim:

1. A herbicidal composition comprising an inert carrier and, as an essential active ingredient, in a quantity toxic to weeds a compound of the formula

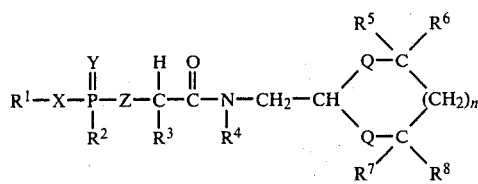

wherein X, Y, Z and Q are each independently selected from the group consisting of oxygen and sulfur; $R^1$ is selected from the group consisting of lower alkyl, and

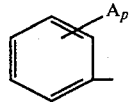

wherein A may be different at different positions and is selected from the group consisting of lower alkyl, lower alkoxy, lower alkylthio, halogen, nitro and cyano, and p is an integer from 0 to 5; $R^2$ is selected from the group consisting of lower alkyl, lower alkoxy, lower alkylthio, amino, lower alkylamino, lower dialkylamino and

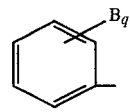

wherein B may be different at different positions and is selected from the group consisting of lower alkyl, lower alkoxy, lower akylthio, halogen, nitro and cyano, and q is an integer from 0 to 5; $R^3$ is selected from the group consisting of hydrogen, lower alkyl and

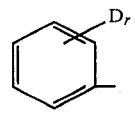

wherein D may be different at different positions and is selected from the group consisting of lower alkyl, lower alkoxy, lower alkylthio, halogen, nitro and cyano, and r is an integer from 0 to 5; $R^4$ is selected from the group consisting of hydrogen, lower alkyl, lower cycloalkyl and

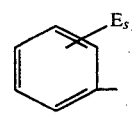

wherein E may be different at different positions and is selected from the group consisting of lower alkyl, lower alkoxy, lower alkylthio, halogen, nitro and cyano, and s is an integer from 0 to 5; $R^5$, $R^6$, $R^7$, and $R^8$ are each independently selected from the group consisting of hydrogen and lower alkyl; and n is an integer from 0 to 3.

2. A method of controlling weeds which comprises contacting said weeds with a herbicidally effective quantity of a herbicidal composition of claim 1.

* * * * *